United States Patent [19]
Wong et al.

[11] Patent Number: 6,166,194
[45] Date of Patent: Dec. 26, 2000

[54] TMPRSS2 IS A TUMOR SUPPRESSOR

[75] Inventors: Alexander K. C. Wong; Sean V. Tavtigian; David H. F. Teng, all of Salt Lake City, Utah

[73] Assignee: Myriad Genetics, Inc., Salt Lake City, Utah

[21] Appl. No.: 09/342,749

[22] Filed: Jun. 29, 1999

Related U.S. Application Data

[60] Provisional application No. 60/091,044, Jun. 29, 1998.

[51] Int. Cl.[7] .......................... C07H 21/00; C07H 21/02; C07H 21/04; C12N 15/00; C12N 15/12
[52] U.S. Cl. .......................... 536/23.5; 536/1; 536/18.7; 536/22.1; 536/23.1
[58] Field of Search ................................ 536/23.1, 18.7

[56] References Cited

U.S. PATENT DOCUMENTS 5,359,047  10/1994  Donahue et al. .
5,710,001  1/1998   Skolnick et al. .

OTHER PUBLICATIONS

Nucleic acid database, Accession #U75329, 1997.

Mollenhauer, J., et al. "DMBT1, a new member of the SRCR superfamily, on chromosome 10q25.3–26.1 is deleted in malignant brain tumors", *Nature Genetics*, Sep. 1997; 17:32–39.

Paoloni–Giacobino, A., et al. "Cloning of the TMPRSS2 Gene, Which Encodes a Novel Serine Protease with Transmembrane, LDLRA, and SRCR Domains and Maps to 21q22.3", *Genomics*, 1997; 44:309–320.

Resnick, D., et al. "The SRCR superfamily: a family reminiscent of the lg superfamily", *Trends Biochem. Sci.*, Jan. 1994; 19:5–8.

Whitney, G.S., et al. "The Membrane–proximal Scavenger Receptor Cysteine–rich Domain of CD6 Contains the Activated Leukocyte Cell Adhesion Molecule Binding Site", *J. Biol. Chem.*, Aug. 4, 1995; 270(31):18187–18190.

*Primary Examiner*—Nancy A. Johnson
*Assistant Examiner*—Alana M. Harris
*Attorney, Agent, or Firm*—Rothwell, Figg, Ernst & Manbeck, P.C.

[57] ABSTRACT

The present invention relates to the relation of the TMPRSS2 gene to human cancers and its use in the diagnosis and prognosis of human cancer. The invention also relates to the therapy of human cancers which have a mutation in the TMPRSS2 gene, including gene therapy, protein replacement therapy and protein mimetics. Finally, the invention relates to the screening of drugs for cancer therapy.

1 Claim, No Drawings

SEQUENCE LISTING

<160> NUMBER OF SEQ ID NOS: 33

<210> SEQ ID NO 1
<211> LENGTH: 1479

-continued

```
<212> TYPE: DNA
<213> ORGANISM: Homo sapiens
<220> FEATURE:
<221> NAME/KEY: CDS
<222> LOCATION: (1)..(1476)
<220> FEATURE:
<221> NAME/KEY: conflict
<222> LOCATION: (724)
<223> OTHER INFORMATION: Listed as T in GenBank Accession NO. U75329
<220> FEATURE:
<221> NAME/KEY: conflict
<222> LOCATION: (985)
<223> OTHER INFORMATION: Listed as C in GenBank Accession No. U75329
<220> FEATURE:
<221> NAME/KEY: conflict
<222> LOCATION: (1347)
<223> OTHER INFORMATION: Listed as C in GenBank Accession No. U75329
<220> FEATURE:
<221> NAME/KEY: conflict
<222> LOCATION: (1466)
<223> OTHER INFORMATION: Listed as A in GenBank Accession No. U75329
<220> FEATURE:
<221> NAME/KEY: conflict
<222> LOCATION: (1471)
<223> OTHER INFORMATION: Listed as A in GenBank Accession No. U75329.
<220> FEATURE:
<221> NAME/KEY: allele
<222> LOCATION: (478)
<223> OTHER INFORMATION: This base can be G or A with G being the more
      common allele. The codon will change from Val to
      Met.
<220> FEATURE:
<221> NAME/KEY: allele
<222> LOCATION: (777)
<223> OTHER INFORMATION: This base can be C or T with C being the more
      common allele.  The codon is unaffected with both
      alleles encoding Gly.
<220> FEATURE:
<221> NAME/KEY: allele
<222> LOCATION: (768)
<223> OTHER INFORMATION: This base can be C or T with C being the more
      common allele.  This is a silent polymorphism.
<220> FEATURE:
<221> NAME/KEY: allele
<222> LOCATION: (834)
<223> OTHER INFORMATION: This base can be C or T with C being the more
      common allele.  This is a silent polymorphism.
<220> FEATURE:
<221> NAME/KEY: allele
<222> LOCATION: (625)
<223> OTHER INFORMATION: This base can be T or A with T being the more
      common allele.  The codon will change from Phe to
      Ile

<400> SEQUENCE: 1 atg gct ttg aac tca ggg tca cca cca gct att gga cct tac tat gaa      48
Met Ala Leu Asn Ser Gly Ser Pro Pro Ala Ile Gly Pro Tyr Tyr Glu
 1               5                  10                  15 aac cat gga tac caa ccg gaa aac ccc tat ccc gca cag ccc act gtg      96
Asn His Gly Tyr Gln Pro Glu Asn Pro Tyr Pro Ala Gln Pro Thr Val
             20                  25                  30 gtc ccc act gtc tac gag gtg cat ccg gct cag tac tac ccg tcc ccc     144
Val Pro Thr Val Tyr Glu Val His Pro Ala Gln Tyr Tyr Pro Ser Pro
         35                  40                  45 gtg ccc cag tac gcc ccg agg gtc ctg acg cag gct tcc aac ccc gtc     192
Val Pro Gln Tyr Ala Pro Arg Val Leu Thr Gln Ala Ser Asn Pro Val
     50                  55                  60 gtc tgc acg cag ccc aaa tcc cca tcc ggg aca gtg tgc acc tca aag     240
Val Cys Thr Gln Pro Lys Ser Pro Ser Gly Thr Val Cys Thr Ser Lys
 65                  70                  75                  80 act aag aaa gca ctg tgc atc acc ttg acc ctg ggg acc ttc ctc gtg     288
Thr Lys Lys Ala Leu Cys Ile Thr Leu Thr Leu Gly Thr Phe Leu Val
                 85                  90                  95
```

```
gga gct gcg ctg gcc gct ggc cta ctc tgg aag ttc atg ggc agc aag       336
Gly Ala Ala Leu Ala Ala Gly Leu Leu Trp Lys Phe Met Gly Ser Lys
            100                 105                 110 tgc tcc aac tct ggg ata gag tgc gac tcc tca ggt acc tgc atc aac       384
Cys Ser Asn Ser Gly Ile Glu Cys Asp Ser Ser Gly Thr Cys Ile Asn
        115                 120                 125 ccc tct aac tgg tgt gat ggc gtg tca cac tgc ccc ggc ggg gag gac       432
Pro Ser Asn Trp Cys Asp Gly Val Ser His Cys Pro Gly Gly Glu Asp
    130                 135                 140 gag aat cgg tgt gtt cgc ctc tac gga cca aac ttc atc ctt cag gtg       480
Glu Asn Arg Cys Val Arg Leu Tyr Gly Pro Asn Phe Ile Leu Gln Val
145                 150                 155                 160 tac tca tct cag agg aag tcc tgg cac cct gtg tgc caa gac gac tgg       528
Tyr Ser Ser Gln Arg Lys Ser Trp His Pro Val Cys Gln Asp Asp Trp
                165                 170                 175 aac gag aac tac ggg cgg gcg gcc tgc agg gac atg ggc tat aag aat       576
Asn Glu Asn Tyr Gly Arg Ala Ala Cys Arg Asp Met Gly Tyr Lys Asn
            180                 185                 190 aat ttt tac tct agc caa gga ata gtg gat gac agc gga tcc acc agc       624
Asn Phe Tyr Ser Ser Gln Gly Ile Val Asp Asp Ser Gly Ser Thr Ser
        195                 200                 205 ttt atg aaa ctg aac aca agt gcc ggc aat gtc gat atc tat aaa aaa       672
Phe Met Lys Leu Asn Thr Ser Ala Gly Asn Val Asp Ile Tyr Lys Lys
    210                 215                 220 ctg tac cac agt gat gcc tgt tct tca aaa gca gtg gtt tct tta cgc       720
Leu Tyr His Ser Asp Ala Cys Ser Ser Lys Ala Val Val Ser Leu Arg
225                 230                 235                 240 tgt ata gcc tgc ggg gtc aac ttg aac tca agc cgc cag agc agg atc       768
Cys Ile Ala Cys Gly Val Asn Leu Asn Ser Ser Arg Gln Ser Arg Ile
                245                 250                 255 gtg ggc ggc gag agc gcg ctc ccg ggg gcc tgg ccc tgg cag gtc agc       816
Val Gly Gly Glu Ser Ala Leu Pro Gly Ala Trp Pro Trp Gln Val Ser
            260                 265                 270 ctg cac gtc cag aac gtc cac gtg tgc gga ggc tcc atc atc acc ccc       864
Leu His Val Gln Asn Val His Val Cys Gly Gly Ser Ile Ile Thr Pro
        275                 280                 285 gag tgg atc gtg aca gcc gcc cac tgc gtg gaa aaa cct ctt aac aat       912
Glu Trp Ile Val Thr Ala Ala His Cys Val Glu Lys Pro Leu Asn Asn
    290                 295                 300 cca tgg cat tgg acg gca ttt gcg ggg att ttg aga caa tct ttc atg       960
Pro Trp His Trp Thr Ala Phe Ala Gly Ile Leu Arg Gln Ser Phe Met
305                 310                 315                 320 ttc tat gga gcc gga tac caa gta gaa aaa gtg att tct cat cca aat      1008
Phe Tyr Gly Ala Gly Tyr Gln Val Glu Lys Val Ile Ser His Pro Asn
                325                 330                 335 tat gac tcc aag acc aag aac aat gac att gcg ctg atg aag ctg cag      1056
Tyr Asp Ser Lys Thr Lys Asn Asn Asp Ile Ala Leu Met Lys Leu Gln
            340                 345                 350 aag cct ctg act ttc aac gac cta gtg aaa cca gtg tgt ctg ccc aac      1104
Lys Pro Leu Thr Phe Asn Asp Leu Val Lys Pro Val Cys Leu Pro Asn
        355                 360                 365 cca ggc atg atg ctg cag cca gaa cag ctc tgc tgg att tcc ggg tgg      1152
Pro Gly Met Met Leu Gln Pro Glu Gln Leu Cys Trp Ile Ser Gly Trp
    370                 375                 380 ggg gcc acc gag gag aaa ggg aag acc tca gaa gtg ctg aac gct gcc      1200
Gly Ala Thr Glu Glu Lys Gly Lys Thr Ser Glu Val Leu Asn Ala Ala
385                 390                 395                 400 aag gtg ctt ctc att gag aca cag aga tgc aac agc aga tat gtc tat      1248
Lys Val Leu Leu Ile Glu Thr Gln Arg Cys Asn Ser Arg Tyr Val Tyr
```

```
                    405                 410                 415
gac aac ctg atc aca cca gcc atg atc tgt gcc ggc ttc ctg cag ggg    1296
Asp Asn Leu Ile Thr Pro Ala Met Ile Cys Ala Gly Phe Leu Gln Gly
                420                 425                 430 aac gtc gat tct tgc cag ggt gac agt gga ggg cct ctg gtc act tcg    1344
Asn Val Asp Ser Cys Gln Gly Asp Ser Gly Gly Pro Leu Val Thr Ser
            435                 440                 445 aag aac aat atc tgg tgg ctg ata ggg gat aca agc tgg ggt tct ggc    1392
Lys Asn Asn Ile Trp Trp Leu Ile Gly Asp Thr Ser Trp Gly Ser Gly
        450                 455                 460 tgt gcc aaa gct tac aga cca gga gtg tac ggg aat gtg atg gta ttc    1440
Cys Ala Lys Ala Tyr Arg Pro Gly Val Tyr Gly Asn Val Met Val Phe
465                 470                 475                 480 acg gac tgg att tat cga caa atg agg gca gac ggc taa                1479
Thr Asp Trp Ile Tyr Arg Gln Met Arg Ala Asp Gly
                485                 490

<210> SEQ ID NO 2
<211> LENGTH: 492
<212> TYPE: PRT
<213> ORGANISM: Homo sapiens

<400> SEQUENCE: 2

Met Ala Leu Asn Ser Gly Ser Pro Pro Ala Ile Gly Pro Tyr Tyr Glu
 1               5                  10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
```

```
                    260                 265                 270
Leu His Val Gln Asn Val His Val Cys Gly Gly Ser Ile Ile Thr Pro
            275                 280                 285
Glu Trp Ile Val Thr Ala Ala His Cys Val Glu Lys Pro Leu Asn Asn
        290                 295                 300
Pro Trp His Trp Thr Ala Phe Ala Gly Ile Leu Arg Gln Ser Phe Met
305                 310                 315                 320
Phe Tyr Gly Ala Gly Tyr Gln Val Glu Lys Val Ile Ser His Pro Asn
                325                 330                 335
Tyr Asp Ser Lys Thr Lys Asn Asn Asp Ile Ala Leu Met Lys Leu Gln
            340                 345                 350
Lys Pro Leu Thr Phe Asn Asp Leu Val Lys Pro Val Cys Leu Pro Asn
        355                 360                 365
Pro Gly Met Met Leu Gln Pro Glu Gln Leu Cys Trp Ile Ser Gly Trp
370                 375                 380
Gly Ala Thr Glu Glu Lys Gly Lys Thr Ser Glu Val Leu Asn Ala Ala
385                 390                 395                 400
Lys Val Leu Leu Ile Glu Thr Gln Arg Cys Asn Ser Arg Tyr Val Tyr
                405                 410                 415
Asp Asn Leu Ile Thr Pro Ala Met Ile Cys Ala Gly Phe Leu Gln Gly
            420                 425                 430
Asn Val Asp Ser Cys Gln Gly Asp Ser Gly Gly Pro Leu Val Thr Ser
        435                 440                 445
Lys Asn Asn Ile Trp Trp Leu Ile Gly Asp Thr Ser Trp Gly Ser Gly
        450                 455                 460
Cys Ala Lys Ala Tyr Arg Pro Gly Val Tyr Gly Asn Val Met Val Phe
465                 470                 475                 480
Thr Asp Trp Ile Tyr Arg Gln Met Arg Ala Asp Gly
                485                 490

<210> SEQ ID NO 3
<211> LENGTH: 21
<212> TYPE: DNA
<213> ORGANISM: Homo sapiens

<400> SEQUENCE: 3
tccacatggt cttcgtcctt g                                         21

<210> SEQ ID NO 4
<211> LENGTH: 21
<212> TYPE: DNA
<213> ORGANISM: Homo sapiens

<400> SEQUENCE: 4
ttgaccgcca gtgcccacaa c                                         21

<210> SEQ ID NO 5
<211> LENGTH: 22
<212> TYPE: DNA
<213> ORGANISM: Homo sapiens

<400> SEQUENCE: 5
cccgtgcatg atttactctt ag                                        22

<210> SEQ ID NO 6
<211> LENGTH: 22
<212> TYPE: DNA
<213> ORGANISM: Homo sapiens
```

```
<400> SEQUENCE: 6
gctccatgct catccaaaat tg                                          22

<210> SEQ ID NO 7
<211> LENGTH: 22
<212> TYPE: DNA
<213> ORGANISM: Homo sapiens

<400> SEQUENCE: 7
aggcaaacgg ctaatccaca tg                                          22

<210> SEQ ID NO 8
<211> LENGTH: 22
<212> TYPE: DNA
<213> ORGANISM: Homo sapiens

<400> SEQUENCE: 8
agtgccaaag ccagacaagt tc                                          22

<210> SEQ ID NO 9
<211> LENGTH: 20
<212> TYPE: DNA
<213> ORGANISM: Homo sapiens

<400> SEQUENCE: 9
acattgggtg gggctcctgg                                             20

<210> SEQ ID NO 10
<211> LENGTH: 22
<212> TYPE: DNA
<213> ORGANISM: Homo sapiens

<400> SEQUENCE: 10
aactgagcat ccttgatttc cc                                          22

<210> SEQ ID NO 11
<211> LENGTH: 22
<212> TYPE: DNA
<213> ORGANISM: Homo sapiens

<400> SEQUENCE: 11
gaccttacta tgaaaaccat gg                                          22

<210> SEQ ID NO 12
<211> LENGTH: 21
<212> TYPE: DNA
<213> ORGANISM: Homo sapiens

<400> SEQUENCE: 12
gggtagtact gagccggatg c                                           21

<210> SEQ ID NO 13
<211> LENGTH: 25
<212> TYPE: DNA
<213> ORGANISM: Homo sapiens

<400> SEQUENCE: 13
gtcatattga acattccaga tacct                                       25

<210> SEQ ID NO 14
<211> LENGTH: 23
<212> TYPE: DNA
```

<213> ORGANISM: Homo sapiens

<400> SEQUENCE: 14
ggtatccggc tccatagaac atg                                    23

<210> SEQ ID NO 15
<211> LENGTH: 39
<212> TYPE: DNA
<213> ORGANISM: Homo sapiens

<400> SEQUENCE: 15
gttttcccag tcacgacgga tacctatcat tactcgatg                   39

<210> SEQ ID NO 16
<211> LENGTH: 40
<212> TYPE: DNA
<213> ORGANISM: Homo sapiens

<400> SEQUENCE: 16
aggaaacagc tatgaccatg tcaaggtgat gcacagtgct                  40

<210> SEQ ID NO 17
<211> LENGTH: 38
<212> TYPE: DNA
<213> ORGANISM: Homo sapiens

<400> SEQUENCE: 17
gttttcccag tcacgacgtc tgcacgcagc ccaaatcc                    38

<210> SEQ ID NO 18
<211> LENGTH: 39
<212> TYPE: DNA
<213> ORGANISM: Homo sapiens

<400> SEQUENCE: 18
aggaaacagc tatgaccatc agggtgccag gacttcctc                   39

<210> SEQ ID NO 19
<211> LENGTH: 38
<212> TYPE: DNA
<213> ORGANISM: Homo sapiens

<400> SEQUENCE: 19
gttttcccag tcacgacggt gtgttcgcct ctacggac                    38

<210> SEQ ID NO 20
<211> LENGTH: 39
<212> TYPE: DNA
<213> ORGANISM: Homo sapiens

<400> SEQUENCE: 20
aggaaacagc tatgaccatt tgagttcaag ttgaccccg                   39

<210> SEQ ID NO 21
<211> LENGTH: 23
<212> TYPE: DNA
<213> ORGANISM: Homo sapiens

<400> SEQUENCE: 21
tgcagggaca tgggctataa gaa                                    23

<210> SEQ ID NO 22
<211> LENGTH: 21

```
<212> TYPE: DNA
<213> ORGANISM: Homo sapiens

<400> SEQUENCE: 22
ttagggagag caggctgggc a                                              21

<210> SEQ ID NO 23
<211> LENGTH: 39
<212> TYPE: DNA
<213> ORGANISM: Homo sapiens

<400> SEQUENCE: 23
gttttcccag tcacgacgcc acagtgatgc ctgttcttc                           39

<210> SEQ ID NO 24
<211> LENGTH: 40
<212> TYPE: DNA
<213> ORGANISM: Homo sapiens

<400> SEQUENCE: 24
aggaaacagc tatgaccatt tgtacttggt atccggctcc                          40

<210> SEQ ID NO 25
<211> LENGTH: 39
<212> TYPE: DNA
<213> ORGANISM: Homo sapiens

<400> SEQUENCE: 25
gttttcccag tcacgacgca tggcattgga cggcatttg                           39

<210> SEQ ID NO 26
<211> LENGTH: 40
<212> TYPE: DNA
<213> ORGANISM: Homo sapiens

<400> SEQUENCE: 26
aggaaacagc tatgaccatc atagacatat ctgctgttgc                          40

<210> SEQ ID NO 27
<211> LENGTH: 39
<212> TYPE: DNA
<213> ORGANISM: Homo sapiens

<400> SEQUENCE: 27
gttttcccag tcacgacgct cagaagtgct gaacgctgc                           39

<210> SEQ ID NO 28
<211> LENGTH: 40
<212> TYPE: DNA
<213> ORGANISM: Homo sapiens

<400> SEQUENCE: 28
aggaaacagc tatgaccatc cagccccatt gttttcttgt                          40

<210> SEQ ID NO 29
<211> LENGTH: 2479
<212> TYPE: DNA
<213> ORGANISM: Homo sapiens

<400> SEQUENCE: 29
gtcatattga acattccaga tacctatcat tactcgatgc tgttgataac agcaagatgg    60
ctttgaactc agggtcacca ccagctattg gaccttacta tgaaaaccat ggataccaac   120
```

-continued

```
cggaaaaccc ctatcccgca cagcccactg tggtccccac tgtctacgag gtgcatccgg      180
ctcagtacta cccgtccccc gtgccccagt acgccccgag ggtcctgacg caggcttcca      240
accccgtcgt ctgcacgcag cccaaatccc catccgggac agtgtgcacc tcaaagacta      300
agaaagcact gtgcatcacc ttgaccctgg ggaccttcct cgtgggagct gcgctggccg      360
ctggcctact ctggaagttc atgggcagca agtgctccaa ctctgggata gagtgcgact      420
cctcaggtac ctgcatcaac ccctctaact ggtgtgatgg cgtgtcacac tgccccggcg      480
gggaggacga gaatcggtgt gttcgcctct acggaccaaa cttcatcctt cagatgtact      540
catctcagag gaagtcctgg caccctgtgt gccaagacga ctggaacgag aactacgggc      600
gggcggcctg cagggacatg ggctataaga ataattttta ctctagccaa ggaatagtgg      660
atgacagcgg atccaccagc tttatgaaac tgaacacaag tgccggcaat gtcgatatct      720
ataaaaaact gtaccacagt gatgcctgtt cttcaaaagc agtggtttct ttacgctgtt      780
tagcctgcgg ggtcaacttg aactcaagcc gccagagcag gatcgtgggc ggtgagagcg      840
cgctcccggg ggcctggccc tgcaggtca gcctgcacgt ccagaacgtc cacgtgtgcg      900
gaggctccat catcaccccc gagtggatcg tgacagccgc ccactgcgtg gaaaaacctc      960
ttaacaatcc atggcattgg acggcatttg cggggatttt gagacaatct ttcatgttct     1020
atggagccgg ataccaagta caaaaagtga tttctcatcc aaattatgac tccaagacca     1080
agaacaatga cattgcgctg atgaagctgc agaagcctct gactttcaac gacctagtga     1140
aaccagtgtg tctgcccaac ccaggcatga tgctgcagcc agaacagctc tgctggattt     1200
ccgggtgggg ggccaccgag gagaaaggga agacctcaga agtgctgaac gctgccaagg     1260
tgcttctcat tgagacacag agatgcaaca gcagatatgt ctatgacaac ctgatcacac     1320
cagccatgat ctgtgccggc ttcctgcagg ggaacgtcga ttcttgccag ggtgacagtg     1380
gagggcctct ggtcacttcg aacaacaata tctggtggct gataggggat acaagctggg     1440
gttctggctg tgccaaagct tacagaccag gagtgtacgg gaatgtgatg gtattcacgg     1500
actggattta tcgacaaatg aaggcaaacg gctaatccac atggtcttcg tccttgacgt     1560
cgttttacaa gaaaacaatg gggctggttt tgcttccccg tgcatgattt actcttagag     1620
atgattcaga ggtcacttca ttttttattaa acagtgaact tgtctggctt tggcactctc     1680
tgccatactg tgcaggctgc agtggctccc ctgcccagcc tgctctccct aaccccttgt     1740
ccgcaagggg tgatggccgg ctggttgtgg gcactggcgg tcaattgtgg aaggaagagg     1800
gttggaggct gcccccattg agatcttcct gctgagtcct ttccaggggc caattttgga     1860
tgagcatgga gctgtcactt tcagctgct ggatgacttg agatgaaaaa ggagagacat     1920
ggaaagggag acagccaggt ggcacctgca gcggctgccc tctgggccca cttggtagtg     1980
tccccagcct acttcacaag gggattttgc tgatgggttc ttagagcctt agcagccctg     2040
gatggtggcc agaaataaag ggaccagccc ttcatgggtg gtgacgtggt agtcacttgt     2100
aaggggaaca gaaacatttt tgttcttatg gggtgagaat atagacagtg cccttggtgc     2160
gagggaagca attgaaaagg aacttgccct gagcactcct ggtgcaggtc tccacctgca     2220
cattgggtgg ggctcctggg agggagactc agccttcctc ctcatcctcc ctgaccctgc     2280
tcctagcacc ctggagagtg aatgcccctt ggtcctggc agggcgccaa gtttggcacc     2340
atgtcggcct cttcaggcct gatagtcatt ggaaattgag gtccatgggg gaaatcaagg     2400
atgctcagtt taaggtacac tgtttccatg ttatgtttct acacattgat ggtggtgacc     2460
ctgagttcaa agccatctt                                                  2479
```

```
<210> SEQ ID NO 30
<211> LENGTH: 18
<212> TYPE: DNA
<213> ORGANISM: Homo sapiens

<400> SEQUENCE: 30
gttttcccag tcacgacg                                                 18

<210> SEQ ID NO 31
<211> LENGTH: 19
<212> TYPE: DNA
<213> ORGANISM: Homo sapiens

<400> SEQUENCE: 31
aggaaacagc tatgaccat                                                19

<210> SEQ ID NO 32
<211> LENGTH: 63
<212> TYPE: DNA
<213> ORGANISM: Artificial Sequence
<220> FEATURE:
<223> OTHER INFORMATION: Description of Artificial Sequence:hypothetical
      nucleic acid

<400> SEQUENCE: 32
accgtagcta cgtacgtata tagaaagggc gcgatcgtcg tcgcgtatga cgacttagca   60
tgc                                                                 63

<210> SEQ ID NO 33
<211> LENGTH: 130
<212> TYPE: DNA
<213> ORGANISM: Artificial Sequence
<220> FEATURE:
<223> OTHER INFORMATION: Description of Artificial Sequence:hypothetical
      nucleic acid

<400> SEQUENCE: 33
accggtagct acgtacgtta tttagaaagg ggtgtgtgtg tgtgtgtaaa ccggggtttt   60
cgggatcgtc cgtcgcgtat gacgacttag ccatgcacgg tatatcgtat taggactagc  120
gattgactag                                                         130
```

TMPRSS2 IS A TUMOR SUPPRESSOR

CROSS-REFERENCE TO RELATED APPLICATION

The present application is related to U.S. provisional application Serial No. 60/091,044, filed Jun. 29, 1998, incorporated herein by reference.

BACKGROUND OF THE INVENTION

The present invention is directed to the TMPRSS2 gene and to methods for diagnosing predisposition to cancer resulting from mutations in TMPRSS2. TMPRSS2 was first identified by Paoloni-Giacobino et al. (1997). It maps to chromosome 21q22.3 and encodes a 492 amino acid long human serine protease which includes three identified domains: transmembrane, LDLRA (LDL receptor class A) and SRCR (scavenger receptor cysteine-rich domain). The transmembrane domain consists of amino acid residues 84–106. The LDLRA domain consists of amino acid residues 113–148. The SRCR domain consists of amino acid residues 149–242.

Because TMPRSS2 belongs to the SRCR superfamily (reviewed in Resnick et al., 1994) and one member of this family, DMBT1, was recently shown to be deleted in malignant brain tumors (Mollenhauer et al., 1998), we decided to examine this gene to determine whether it is related to any cancer. The biochemical function of the SRCR domain is not well established. This domain appears to be involved with binding to other cell-surface or extracellular molecules. For example, the SRCR domain of a cell surface protein CD6 binds to ALCAM (activated leukocyte cell adhesion molecule) (Whitney et al., 1995).

The genetics of cancer is complicated, involving multiple dominant, positive regulators of the transformed state (oncogenes) as well as multiple recessive, negative regulators (tumor suppressor genes). Over one hundred oncogenes have been characterized. The number of tumor suppressor genes is expected to increase beyond fifty (Knudson, 1993).

The involvement of so many genes underscores the complexity of the growth control mechanisms that operate in cells to maintain the integrity of normal tissue. This complexity is manifested in another way. So far, no single gene has been shown to participate in the development of all, or even the majority of human cancers. The most common oncogenic mutations are in the H-ras gene, found in 10–15% of all solid tumors (Anderson et al., 1992). The most frequently mutated tumor suppressor gene is the p53 gene, mutated in roughly 50% of all tumors. Without a target that is common to all transformed cells, the dream of a "magic bullet" that can destroy or revert cancer cells while leaving normal tissue unharmed is improbable. The hope for a new generation of specifically targeted antitumor drugs may rest on the ability to identify tumor suppressor genes or oncogenes that play general roles in control of cell division.

Some of the tumor suppressor genes, which have been cloned and characterized, influence susceptibility to: 1) retinoblastoma (RB1); 2) Wilms' tumor (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); and 8) Multiple endocrine neoplasia type 2A (MEN2A).

Tumor suppressor loci that have been mapped genetically but not yet isolated include genes for: Multiple endocrine neoplasia type 1 (MEN1); Lynch cancer family syndrome 2 (LCFS2); Neuroblastoma (NB); Basal cell nevus syndrome (BCNS); Beckwith-Wiedemann syndrome (BWS); Renal cell carcinoma (RCC); Tuberous sclerosis 1 (TSC1); and Tuberous sclerosis 2 (TSC2). The tumor suppressor genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), and others with no obvious similarity to known proteins (APC and VHL).

In many cases, the tumor suppressor gene originally identified through genetic studies has been shown in some sporadic tumors to be lost or mutated. This result suggests that regions of chromosomal aberration may signify the position of important tumor suppressor genes involved both in genetic predisposition to cancer and in sporadic cancer.

One of the hallmarks of several tumor suppressor genes characterized to date is that they are deleted at high frequency in certain tumor types. The deletions often involve loss of a single allele, a so-called loss of heterozygosity (LOH), but may also involve homozygous deletion of both alleles. For LOH, the remaining allele is presumed to be nonfunctional, either because of a preexisting inherited mutation, or because of a secondary sporadic mutation. Whereas LOH events commonly involve chromosomal deletions spanning many megabases of DNA, homozygous deletions are relatively small in size, probably due to the presence of essential genes in their proximity. Indeed, the identification of tumor suppressor genes has been facilitated by the discovery of homozygous deletions present within the genomes of cancer cell lines and xenografts; examples include p16 (Kamb et al., 1994), DPC4 (Hahn et al., 1996), BRCA2 (Wooster et al., 1995; Tavtigian et al., 1996) and MMAC1/PTEN (Steck et al., 1997; Li et al., 1997).

Melanoma is a common cancer afflicting one in every hundred Americans (American Cancer Society, 1992). Environmental influences, such as exposure to ultraviolet light, play a large role in melanoma incidence, but heredity is also a contributing factor. A gene for familial melanoma, MLM, has been mapped to chromosome 9p21 (Cannon-Albright et al., 1992; Nancarrow et al., 1993; Gruis et al., 1993; Goldstein et al., 1994). Possession of a single predisposing allele at the MLM locus increases the probability that an individual will develop melanoma by up to approximately 50-fold. MLM belongs to the growing family of suspected tumor suppressor genes. Predisposition to melanoma is inherited as a dominant Mendelian trait, yet predisposing mutations in MLM are thought to act as somatic recessive alleles in the manner originally proposed by Knudson (1971). In a predisposed individual who carries one wild-type and one mutant MLM allele, dividing cells undergo secondary mutational events that involve loss or inactivation of the wild-type copy of MLM, thereby uncovering the inherited mutant MLM allele. Conversely, a single wild-type copy of the gene prevents the onset of malignancy.

Chromosomal aberrations in the vicinity of MLM at 9p21 have been extensively characterized in several different tumor types, including glioma cell lines, non-small cell lung lines and acute lymphoblastic leukemia lines (Olopade et al., 1992; Olopade et al., 1993; Lukeis et al., 1990; Diaz et al., 1988; Middleton et al., 1991; Fountain et al., 1992; Cheng et al., 1993; James et al., 1993). Thus, based on the frequency of 9p21 chromosomal abnormalities in non-melanoma tumor cells, it is probable the MLM region contains a gene (or genes) that participates at least in the progression of several different tumor types. These events involve LOH as well as a high frequency of homozygous deletion.

Cells in tissues have only three serious options in life—they can grow and divide, not grow but stay alive, or die by apoptosis. Tumors may arise either by inappropriate growth and division or by cells failing to die when they should. One of the mechanisms for controlling tumor growth might involve direct regulation of the cell cycle. For example, genes that control the decision to initiate DNA replication are attractive candidates for oncogenes or tumor suppressor genes, depending on whether they have a stimulatory or inhibitory role in the process. Progression of eukaryotic cells through the cell cycle ($G_1$, S, $G_2$ and M phases) is governed by the sequential formation, activation and subsequent inactivation of a series of cyclin/cyclin-dependent kinase (Cdk) complexes. Cyclin D's/Cdk2,4,5, Cyclin E/Cdk2, Cyclin A/Cdk2 and Cyclin B/A/Cdk2 have been shown to be involved in this process. Cyclin D's and Cdk2, Cdk4 and Cdk5 have been implicated in the transition from $G_1$ to S; that is, when cells grow and decide whether to begin DNA replication. Additional cell cycle control elements have recently been discovered. These elements are inhibitors of Cdks (Cdk inhibitors, CkI), and include Far1, p21, p40, p20 and p16 (Marx, 1994; Nasmyth and Hunt, 1993).

Recently, several oncogenes and tumor suppressor genes have been found to participate directly in the cell cycle. For example, one of the cyclins (proteins that promote DNA replication) has been implicated as an oncogene (Motokura et al., 1991; Lanunie et al., 1991; Withers et al., 1991; Rosenberg et al., 1991), and tumor suppressor Rb interacts with the primary cyclin-binding partners, the Cdks (Ewen et al., 1993). Identification of a melanoma susceptibility locus would open the way for genetic screening of individuals to assess, for example, the increased risk of cancer due to sunlight exposure. A family of multiple tumor suppressor (MTS) genes has also been found and studied (Kamb et al., 1994; Liu et al., 1995b; Jiang et al., 1995; Stone et al., 1995a; Stone et al., 1995b; Gruis et al., 1995; Liu et al., 1995a; Hannon and Beach, 1994; Serrano et al., 1993). The MTS genes may also predispose to a large number of other cancer sites, including but not limited to, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. In addition, since MTS influences progression of several different tumor types, it should be useful for determining prognosis in cancer patients. Thus, MTS may serve as the basis for development of very important diagnostic tests, one capable of predicting the predisposition to cancer, such as melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum, and one capable of predicting the prognosis of cancer. Furthermore, since MTS is involved in the progression of multiple tumor types, MTS may provide the means, either directly or indirectly, for a general anti-cancer therapy by virtue of its ability to suppress tumor growth. For example, restoration of the normal MTS function to a tumor cell may transmute the cell into non-malignancy.

Mitogen-activated protein kinases (MAPKs) function in signal transduction pathways that are involved in controlling key cellular processes in many organisms. Several MAPKKK-MAPKK-MAPK pathways have been identified in mammals (Waskiewicz and Cooper, 1995; Kyriakis and Avruch, 1996). Stimulation of these MAPK pathways by different extracellular factors or environmental stresses results in the downstream regulation of transcription factors that elicit appropriate cellular responses. A mammalian member of this kinase family, MKK4/JNKK1/SEK1, has been reported to link upstream MEKK1 to downstream SAPK/JNK1 and p38 MAP kinase (Dérijard et al., 1995; Lin et al., 1995; Yan et al., 1994). This MAPK pathway has been implicated in the signal transduction of cytokine- and stress-induced apoptosis in a variety of cell types (Xia et al., 1995; Chen et al., 1996; Johnson et al., 1996; Verheij et al., 1996; Cuvillier et al., 1996).

The TMPRSS2 gene is shown by the instant disclosure to be yet one more tumor suppressor gene. The pancreatic carcinoma cell line BxPC3 is shown to contain a homozygous deletion of this gene.

The publications and other materials used herein to illuminate the background of the invention or provide additional details respecting the practice, are incorporated by reference, and for convenience are respectively grouped in the appended List of References.

SUMMARY OF THE INVENTION

The cell line BxPC3, which is a pancreatic carcinoma cell line, is shown to have a homozygous deletion of TMPRSS2. A panel of 186 tumor cell lines was examined for homozygous deletion of this gene, with BxPC3 being the sole cell line which contained such a deletion. The gene has also been sequenced for 64 of these cell lines and the sequence was determined to differ at 5 nucleotides from the reported sequence (Paoloni-Giacobino et al., 1997; GenBank Accession No. U75329). The sequencing led to the determination of various alleles and polymorphisms. One missense variant was found in a heterozygous form in breast tumor cell line BT483.

SUMMARY OF SEQUENCE LISTING

SEQ ID NO:1 is the complete coding region for TMPRSS2.

SEQ ID NO:2 is the complete amino acid sequence for TMPRSS2.

SEQ ID NOs:3–12 are five sets of primer pairs for performing PCR used for screening for homozygous deletions of TMPRSS2 (see Table II).

SEQ ID NOs:13–28 are primers used in performing PCR amplify TMPRSS2 for sequencing. SEQ ID NOs:13–14 and 21–22 are primer pairs used for a primary round of PCR and SEQ ID NOs:15–16, 17–18, 19–20, 23–24, 25–26 and 27–28 are primer pairs for secondary rounds of PCR (See Table III).

SEQ ID NO:29 is identical to GenBank Accession No. U75329 and encodes TMPRSS2 and includes 56 bases 5' of the translation start as well as 944 bases 3' of the stop codon.

SEQ ID NOs:30 and 31 are M13 tails which have been placed onto primers used in secondary rounds of PCR.

SEQ ID NOs:32–33 are hypothetical nucleic acids used to demonstrate a method of calculating percent homology between two nucleic acids.

DETAILED DESCRIPTION OF THE INVENTION

The present invention relates to the nucleic acid sequence of the TMPRSS2 gene and the relationship of this gene to human cancers. The invention further relates to the use in the diagnosis and prognosis of human cancer by analysis of the TMPRSS2 gene. The invention further relates to alterations in the TMPRSS2 gene. The invention also relates to the therapy of human cancers which have a mutation in or deletion of the TMPRSS2 gene, including gene therapy, protein replacement therapy and protein mimetics. Finally, the invention relates to the screening of drugs for cancer therapy.

The present invention provides an isolated polynucleotide comprising all, or a portion of the TMPRSS2 locus or of an altered TMPRSS2 locus, preferably at least eight bases and not more than about 100 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the TMPRSS2 locus or its expression product in an analyte. Such methods may further comprise the step of amplifying the portion of the TMPRSS2 locus, and may further include a step of providing a set of polynucleotides which are primers for amplification of said portion of the TMPRSS2 locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the TMPRSS2 locus.

The present invention also provides kits for detecting in an analyte a polynucleotide comprising a portion of the TMPRSS2 locus, the kits comprising a polynucleotide complementary to the portion of the TMPRSS2 locus packaged in a suitable container, and instructions for their use.

The present invention further provides methods of preparing a polynucleotide comprising polymerizing nucleotides to yield a sequence comprised of at least eight consecutive nucleotides of the TMPRSS2 locus; and methods of preparing a polypeptide comprising polymerizing amino acids to yield a sequence comprising at least five amino acids encoded within the TMPRSS2 locus.

In addition, the present invention provides methods of screening drugs for cancer therapy to identify suitable drugs for restoring TMPRSS2 gene product function.

Finally, the present invention provides the means necessary for production of gene-based therapies directed at cancer cells. These therapeutic agents may take the form of polynucleotides comprising all or a portion of the TMPRSS2 locus placed in appropriate vectors or delivered to target cells in more direct ways such that the function of the TMPRSS2 protein is reconstituted. Therapeutic agents may also take the form of polypeptides based on either a portion of, or the entire protein sequence of TMPRSS2. These may functionally replace the activity of TMPRSS2 in vivo.

It is a discovery of the present invention that the TMPRSS2 locus predisposes individuals to pancreatic cancers. The TMPRSS2 locus was first recognized as containing a tumor suppressor gene when it was noted to be part of a homozygous deletion in a pancreatic tumor cell line called BxPC3.

According to the diagnostic and prognostic method of the present invention, alteration of the wild-type TMPRSS2 locus is detected. In addition, the method can be performed by detecting the wild-type TMPRSS2 locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are mutated, then a late neoplastic state is indicated. A TMPRSS2 allele which is not deleted (e.g., that found on the sister chromosome to a chromosome carrying a TMPRSS2 deletion) can be screened for other mutations, such as insertions, small deletions, and point mutations. It is believed that many mutations found in tumor tissues will be those leading to decreased expression of the TMPRSS2 gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the TMPRSS2 gene product, or a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology.

Predisposition to cancers, such as pancreatic and the other cancers identified herein, can be ascertained by testing any tissue of a human for mutations of the TMPRSS2 gene. For example, a person who has inherited a germline TMPRSS2 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic fluid for mutations of the TMPRSS2 gene. Alteration of a wild-type TMPRSS2 allele, whether, for example, by point mutation or by deletion, can be detected by any of the means discussed herein.

In order to detect the alteration of the wild-type TMPRSS2 gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably a large number of restriction enzymes. Each blot contains a series of normal individuals and a series of cancer cases, tumors, or both. Southern blots displaying hybridizing fragments (differing in length from control DNA when probed with sequences near or including the TMPRSS2 locus) indicate a possible mutation. If restriction enzymes which produce very large restriction fragments are used, then pulsed field gel electrophoresis ("PFGE") is employed.

Detection of point mutations may be accomplished by molecular cloning of the TMPRSS2 allele and sequencing that allele using techniques well known in the art. Alternatively, the gene sequences can be amplified, using known techniques, directly from a genomic DNA preparation from the tumor tissue. The DNA sequence of the amplified sequences can then be determined.

There are six well known methods for a more complete, yet still indirect, test for confirming the presence of a susceptibility allele: 1) single stranded conformation analysis ("SSCA") (Orita et al., 1989); 2) denaturing gradient gel electrophoresis ("DGGE") (Wartell et al., 1990; Sheffield et al., 1989); 3) RNase protection assays (Finkelstein et al., 1990; Kinszler et al., 1991); 4) allele-specific oligonucleotides ("ASOs") (Conner et al., 1983); 5) the use of proteins which recognize nucleotide mismatches, such as the *E. coli* mutS protein (Modrich, 1991); and 6) allele-specific PCR (Ruano and Kidd, 1989). For allele-specific PCR, primers are used which hybridize at their 3' ends to a particular TMPRSS2 mutation. If the particular TMPRSS2 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the TMPRSS2 mutation found in that individual. Other techniques for detecting insertions and deletions as known in the art can be used.

In the first three methods (i.e., SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type TMPRSS2 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the TMPRSS2 mRNA or gene but can be a segment of either. If the riboprobe comprises only a segment of the TMPRSS2 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the TMPRSS2 gene can also be detected using Southern hybridization, especially if the changes are gross rearrangements, such as deletions and insertions.

DNA sequences of the TMPRSS2 gene which have been amplified by use of PCR may also be screened using allele-specific probes. These probes are nucleic acid oligomers, each of which contains a region of the TMPRSS2 gene sequence harboring a known mutation. For example, one oligomer may be about 30 nucleotides in length, corresponding to a portion of the TMPRSS2 gene sequence. By use of a battery of such allele-specific probes, PCR amplification products can be screened to identify the presence of a previously identified mutation in the TMPRSS2 gene. Hybridization of allele-specific probes with amplified TMPRSS2 sequences can be performed, for example, on a nylon filter. Hybridization to a particular probe under stringent hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic TMPRSS2 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of TMPRSS2 can be detected by examining the non-coding regions, such as introns and regulatory sequences near or within the TMPRSS2 gene. An early indication that mutations in noncoding regions are important may come from Northern blot experiments that reveal messenger RNA molecules of abnormal size or abundance in cancer patients as compared to control individuals.

Alteration of TMPRSS2 mRNA expression can be detected by any techniques known in the art. These include Northern blot analysis, PCR amplification, RNase protection and the microchip method discussed above. Diminished mRNA expression indicates an alteration of the wild-type TMPRSS2 gene. Alteration of wild-type TMPRSS2 genes can also be detected by screening for alteration of wild-type TMPRSS2 protein. For example, monoclonal antibodies immunoreactive with TMPRSS2 can be used to screen a tissue. Lack of cognate antigen would indicate a TMPRSS2 mutation. Antibodies specific for products of mutant alleles could also be used to detect mutant TMPRSS2 gene product. Such immunological assays can be done in any convenient formats known in the art. These include Western blots, immunohistochemical assays and ELISA assays. Any means for detecting an altered TMPRSS2 protein can be used to detect alteration of wild-type TMPRSS2 genes. Functional assays can be used. For example, TMPRSS2 is a serine protease (Paoloni-Giacobino et al., 1997) and an assay for this protease activity can be performed. TMPRSS2 also includes an LDL receptor domain and will bind low density lipoproteins as well as calcium (Paoloni-Giacobino et al., 1997) and assays for these types of binding can also be performed.

Mutant TMPRSS2 genes or gene products can also be detected in other human body samples, such as serum, stool, urine and sputum. The same techniques discussed above for detection of mutant TMPRSS2 genes or gene products in tissues can be applied to other body samples. Cancer cells are sloughed off from tumors and appear in such body samples. In addition, the TMPRSS2 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant TMPRSS2 genes or gene products.

The methods of diagnosis of the present invention are applicable to any tumor in which TMPRSS2 has a role in tumorigenesis. The diagnostic method of the present invention is useful for clinicians, so they can decide upon an appropriate course of treatment.

The primer pairs of the present invention are useful for determination of the nucleotide sequence of a particular TMPRSS2 allele using the PCR. The pairs of single-stranded DNA primers can be annealed to sequences within or surrounding the TMPRSS2 gene in order to prime amplifying DNA synthesis of the TMPRSS2 gene itself. A complete set of these primers allows synthesis of all of the nucleotides of the TMPRSS2 gene coding sequences, i.e., the exons. The set of primers preferably allows synthesis of both intron and exon sequences. Allele-specific primers can also be used. Such primers anneal only to particular TMPRSS2 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from TMPRSS2 sequences or sequences adjacent to TMPRSS2, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of TMPRSS2 shown in SEQ ID NO:1 design of particular primers is well within the skill of the art.

The nucleic acid probes provided by the present invention are useful for a number of purposes. They can be used in Southern hybridization to genomic DNA and in the RNase protection method for detecting point mutations. The probes can be used to detect PCR amplification products. They may also be used to detect mismatches with the TMPRSS2 gene or mRNA using other techniques.

Mutations which interfere with the function of the TMPRSS2 gene product are involved in the pathogenesis of cancer. Thus, the presence of an altered (or a mutant) TMPRSS2 gene which produces a protein having a loss of function, or altered function, or the lack of this protein, directly increases the risk of cancer. In order to detect a TMPRSS2 gene mutation, a biological sample is prepared and analyzed for a difference between the sequence of the allele being analyzed and the sequence of the wild-type allele. Mutant TMPRSS2 alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele.

The mutations, especially those which lead to an altered function of the protein, are then used for the diagnostic and prognostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu and Wallace, 1989 (for LCR). Reagents and hardware for conducting PCR are commercially available. Primers useful to amplify sequences from the TMPRSS2 region are preferably complementary to, and hybridize specifically to, sequences in the TMPRSS2 region or in regions that flank a target region therein. TMPRSS2 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the TMPRSS2 polypeptides and fragments thereof or to polynucleotide sequences from the TMPRSS2 region, particularly from the TMPRSS2 locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the TMPRSS2 polypeptide or fragment. Monoclonal antibodies may be made by injecting mice with the protein polypeptides, fusion proteins or fragments thereof. Monoclonal antibodies will be screened by ELISA and tested for specific immunoreactivity with TMPRSS2 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art.

For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"TMPRSS2 Allele" refers to normal alleles of the TMPRSS2 locus as well as alleles carrying variations that predispose individuals to develop cancer. Such predisposing alleles are also called "TMPRSS2 susceptibility alleles".

"TMPRSS2," "TMPRSS2 gene," "TMPRSS2 Nucleic Acids" or "TMPRSS2 Polynucleotide" refers to polynucleotides, all of which are in the TMPRSS2 region, that are likely to be expressed in normal tissue, certain alleles of which predispose an individual to develop breast, pancreatic, colorectal or testicular cancer. Mutations at the TMPRSS2 locus may be involved in the initiation and/or progression of other types of tumors. The locus is indicated in part by mutations that predispose individuals to develop cancer. These mutations fall within the TMPRSS2 region described infra. The TMPRSS2 locus is intended to include coding sequences, intervening sequences and regulatory elements controlling transcription and/or translation. The TMPRSS2 locus is intended to include all allelic variations of the DNA sequence.

These terms, when applied to a nucleic acid, refer to a nucleic acid which encodes a TMPRSS2 polypeptide, fragment, homolog or variant, including, e.g., protein fusions or deletions. The nucleic acids of the present invention will possess a sequence which is either derived from, or substantially similar to, a natural TMPRSS2-encoding gene or one having substantial homology with a natural TMPRSS2-encoding gene or a portion thereof. The cDNA for TMPRSS2 is shown in SEQ ID NO:1 and the encoded polypeptide sequence is given as SEQ ID NO:2.

The TMPRSS2 gene or nucleic acid includes normal alleles of the TMPRSS2 gene, both silent alleles having no effect on the amino acid sequence of the TMPRSS2 polypeptide and alleles leading to amino acid sequence variants of the TMPRSS2 polypeptide that do not substantially affect its function. These terms also include alleles having one or more mutations which adversely affect the function of the TMPRSS2 polypeptide. A mutation may be a change in the TMPRSS2 nucleic acid sequence which produces a deleterious change in the amino acid sequence of the TMPRSS2 polypeptide, resulting in partial or complete loss of TMPRSS2 function, or may be a change in the nucleic acid sequence which results in the loss of effective TMPRSS2 expression or the production of aberrant forms of the TMPRSS2 polypeptide.

The TMPRSS2 nucleic acid may be that shown in SEQ ID NO:1, or it may be an allele as described above, or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO:1 yet encode a polypeptide with the same amino acid sequence as shown in SEQ ID NO:2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The TMPRSS2 gene also refers to (a) any DNA sequence that (i) hybridizes to the complement of the DNA sequences that encode the amino acid sequence set forth in SEQ ID NO:2 under highly stringent conditions (Ausubel et al., 1992) and (ii) encodes a gene product functionally equivalent to TMPRSS2, or (b) any DNA sequence that (i) hybridizes to the complement of the DNA sequences that encode the amino acid sequence set forth in SEQ ID NO:2 under less stringent conditions, such as moderately stringent conditions (Ausubel et al., 1992), and (ii) encodes a gene product functionally equivalent to TMPRSS2. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the TMPRSS2 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a TMPRSS2-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotech, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, the terms "TMPRSS2 locus", "TMPRSS2 allele" and "TMPRSS2 region" all refer to the double-stranded DNA comprising the locus, allele, or region, as well as either of the single-stranded DNAs comprising the locus, allele or region.

As used herein, a "portion" of the TMPRSS2 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these values (e.g., 9, 10, 11, 16, 23, 30, 38, 50, 72, 121, etc, nucleotides), or nucleic acids having more than 500 nucleotides, or any number of nucleotides between 500 and the number shown in SEQ ID NO:1. The present invention includes all novel nucleic acids having at least 8 nucleotides derived from SEQ ID NO:1, its complement or functionally equivalent nucleic acid sequences. The present invention does not include nucleic acids which exist in the prior art. That is, the present invention includes all nucleic acids having at least 8 nucleotides derived from SEQ ID NO:1 with the proviso that it does not include nucleic acids existing in the prior art.

"TMPRSS2 protein" or "TMPRSS2 polypeptide" refers to a protein or polypeptide encoded by the TMPRSS2 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native TMPRSS2 sequence, preferably in excess of about 90%, and more preferably at least about 95% homologous. Also included are proteins encoded by DNAs which hybridize under high or low stringency conditions to TMPRSS2-encoding nucleic acids and closely related polypeptides or proteins retrieved by antisera to the TMPRSS2 protein.

The TMPRSS2 polypeptide may be that shown in SEQ ID NO:2 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the TMPRSS2 polypeptide. Such polypeptides may have an amino acid sequence which differs from that set forth in SEQ ID NO:2 by one or more of addition, substitution, deletion or insertion of one or more amino acids. Preferred such polypeptides have TMPRSS2 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the TMPRSS2 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to ajuxtaposition wherein the components so described are in a relationship permitting them to function in their intended manner. For instance, a promoter is operably linked to a coding sequence if the promoter affects its transcription or expression.

The term "peptide mimetic" or "mimetic" is intended to refer to a substance which has the essential biological activity of the TMPRSS2 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural TMPRSS2 polypeptide.

"Probes". Polynucleotide polymorphisms associated with TMPRSS2 alleles which predispose to certain cancers or are associated with most cancers are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a TMPRSS2 susceptibility allele.

Probes for TMPRSS2 alleles may be derived from the sequences of the TMPRSS2 region, its cDNA, functionally equivalent sequences, or the complements thereof. The probes may be of any suitable length, which span all or a portion of the TMPRSS2 region, and which allow specific hybridization to the TMPRSS2 region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 Kb, usually fewer than about 1.0 Kb, from a polynucleotide sequence encoding TMPRSS2 are preferred as probes. This definition therefore includes probes of sizes 8 nucleotides through 9000 nucleotides. Thus, this definition includes probes of 8, 12, 15, 20, 25, 40, 60, 80, 100, 200, 300, 400, 500 nucleotides, or probes having any number of nucleotides within these values (e.g., 9, 10, 11, 16, 23, 30, 38, 50, 72, 121, etc, nucleotides), or probes having more than 500 nucleotides, or any number of nucleotides between 500 and the number shown in SEQ ID NO:1. The probes may also be used to determine whether mRNA encoding TMPRSS2 is present in a cell or tissue. The present invention includes all novel probes having at least 8 nucleotides derived from SEQ ID NO:1, its complement or functionally equivalent nucleic acid sequences. The present invention does not include probes which exist in the prior art. That is, the present invention includes all probes having at least 8 nucleotides derived from SEQ ID NO:1 with the proviso that it does not include probes existing in the prior art.

Similar considerations and nucleotide lengths are also applicable to primers which may be used for the amplification of all or part of the TMPRSS2 gene. Thus, a definition for primers includes primers of 8, 12, 15, 20, 25, 40, 60, 80, 100, 200, 300, 400, 500 nucleotides, or primers having any number of nucleotides within these values (e.g., 9, 10, 11, 16, 23, 30, 38, 50, 72, 121, etc, nucleotides), or primers having more than 500 nucleotides, or any number of nucleotides between 500 and 9000. The primers may also be used to determine whether mRNA encoding TMPRSS2 is present in a cell or tissue. The present invention includes all novel primers having at least 8 nucleotides derived from the TMPRSS2 locus for amplifying the TMPRSS2 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for TMPRSS2 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands, which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 or Ausubel et al., 1992.

Besides substantially full-length polypeptides, the present invention provides for biologically active fragments of the polypeptides. Significant biological activities include protease activity, LDL and calcium binding activity, immunological activity and other biological activities characteristic of polypeptides with SRCR domains. Immunological activities include both immunogenic function in a target immune system, as well as sharing of immunological epitopes for binding, serving as either a competitor or substitute antigen for an epitope of the TMPRSS2 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for TMPRSS2 polypeptides or fragments thereof is described below.

The present invention also provides for fusion polypeptides, comprising TMPRSS2 polypeptides and fragments. Homologous polypeptides may be fusions between two or more TMPRSS2 polypeptide sequences or between the sequences of TMPRSS2 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See, e.g., Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the TMPRSS2 polypeptides from other biological material, such as from cells transformed with recombinant nucleic acids encoding TMPRSS2, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis or a protein sample, followed by visualizing a single polypeptide band upon staining the gel. For certain purposes, higher resolution may be provided by using HPLC or other means well known in the art for purification utilized.

A TMPRSS2 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 Kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

To determine identity between two different nucleic acids, the percent identity is to be determined using the BLASTN program "BLAST 2 sequences". This program is available for public use from the National Center for Biotechnology Information (NCBI) over the Internet (http://www.ncbi.nlm.nih.gov/gorf/b12.html) (Altschul et al., 1997). The parameters to be used are whatever combination of the following yields the highest calculated percent identity (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—1, 2, 3, 4 or 5 (5)
Extension gap penalty—0 or 1 (1)
Gap x_dropoff—50
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining identity herein, the percent identity refers to the shorter of the two sequences being compared. If any one region is shown in different alignments with differing percent identities, the alignments which yield the greatest identity are to be used. The averaging is to be performed as in this example of SEQ ID NOs:32 and 33.

5'-ACCGTAGCTACGTACGTATATAGAAAGGGCGCGA TCGTCGTCGCGTATGACGAC TTAGCATGC-3' (SEQ ID NO:32)

5'-ACCGGTAGCTACGTACGTTATTTAGAAAGGGGTG TGTGTGTGTGTGTAAACCGGG GTTTTCGG-GATCGTCCGTCGCGTATGACGACTTAGC-CATGCACGGTATATCGTATTA GGACTAGCGATTGACTAG-3' (SEQ ID NO:33)

The program "BLAST 2 Sequences" shows differing alignments of these two nucleic acids depending upon the parameters which are selected. As examples, four sets of parameters were selected for comparing SEQ ID NOs:32 and 33, with the results shown in Table I. It is to be noted that none of the sets of parameters selected as shown in Table I is necessarily the best set of parameters for comparing these sequences. The percent identity is calculated by multiplying for each region showing identity the fraction of bases of the shorter strand within a region times the percent identity for that region and adding all of these together. For example, using the first set of parameters shown in Table I, SEQ ID NO:32 is the short sequence (63 bases), and two regions of identity are shown, the first encompassing bases 4–29 (26 bases) of SEQ ID NO:32 with 92% identity to SEQ ID NO:33 and the second encompassing bases 39–59 (21 bases) of SEQ ID NO:32 with 100% identity to SEQ ID NO:33. Bases 1–3, 30–38 and 60–63 (16 bases) are not shown as having any identity with SEQ ID NO:33. Percent identity is calculated as: (26/63)(92)+(21/63)(100)+(16/63)(0)=71.3% identity. The percents of identity calculated using each of the four sets of parameters shown are listed in Table I. Several other combinations of parameters are possible, but they are not listed for the sake of brevity. It is seen that each set of parameters resulted in a different calculated percent identity. Because the result yielding the highest percent identity is to be used, based solely on these four sets of parameters one would state that SEQ ID NOs:32 and 33 have 87.1% identity. Again it is to be noted that use of other parameters may show an even higher identity for SEQ ID NOs:32 and 33, but for brevity not all the possible results are shown.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about eight nucleotides, usually at least about 20 nucleotides, more usually at least about 24 nucleotides, typically at least about 28 nucleotides, more typically at least about 32 nucleotides, and preferably at least about 36 or more nucleotides.

TABLE I

| | Parameter Values | | | | | |
|---|---|---|---|---|---|---|
| Match | Mismatch | Open Gap | Extension Gap | Regions of identity (%) | | Identity |
| 1 | −2 | 5 | 1 | 4–29 of 32 and 5–31 of 33 (92%) | 39–59 of 32 and 71–91 of 33 (100%) | 71.3 |
| 1 | −2 | 2 | 1 | 4–29 of 32 and 5–31 of 33 (92%) | 33–63 of 32 and 64–96 of 33 (93%) | 83.7 |
| 1 | −1 | 5 | 1 | — | 30–59 of 32 and 61–91 of 33 (93%) | 44.3 |
| 1 | −1 | 2 | 1 | 4–29 of 32 and 5–31 of 33 (92%) | 30–63 of 32 and 61–96 of 33 (91%) | 87.1 |

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type TMPRSS2 nucleic acid or wild-type TMPRSS2 polypeptide. The modified polypeptide will be substantially homologous to the wild-type TMPRSS2 polypeptide and will have substantially the same function. The modified polypeptide may have an altered amino acid sequence and/or may contain modified amino acids. The modified polypeptide may have other useful properties, such as a longer half-life. The protease activity of the modified polypeptide may be substantially the same as the activity of the wild-type TMPRSS2 polypeptide. Alternatively, the protease activity of the modified polypeptide may be higher or lower than the activity of the wild-type TMPRSS2 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type TMPRSS2 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Carruthers, 1981 or the triester method according to Matteucci et al., 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with TMPRSS2 genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. No. 5,691,198.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, T. Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the TMPRSS2 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines. An example of a commonly used insect cell line is SF9. However, it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of TMPRSS2 polypeptides.

Antisense polynucleotide sequences are useful in preventing or diminishing the expression of the TMPRSS2 locus, as will be appreciated by those skilled in the art. For example, polynucleotide vectors containing all or a portion of the TMPRSS2 locus or other sequences from the TMPRSS2 region (particularly those flanking the TMPRSS2 locus) may be placed under the control of a promoter in an antisense orientation and introduced into a cell. Expression of such an antisense construct within a cell will interfere with TMPRSS2 transcription and/or translation and/or replication.

Methods of Use: Nucleic Acid Diagnosis and Diagnostic Kits

In order to detect the presence of a TMPRSS2 allele predisposing an individual to cancer, a biological sample such as blood is prepared and analyzed for the presence or absence of susceptibility alleles of TMPRSS2. In order to detect the presence of neoplasia, the progression toward malignancy of a precursor lesion, or as a prognostic indicator, a biological sample of the lesion is prepared and analyzed for the presence or absence of neoplastic alleles of TMPRSS2. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant TMPRSS2 sequences, e.g., by PCR, followed by DNA sequence analysis. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

Non-PCR based screening assays are also contemplated in this invention. An exemplary non-PCR based procedure is provided in Example 4. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding TMPRSS2. Allele specific probes are also contemplated within the scope of this example.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby, et al., 1977 and Nguyen, et al. (1992).

It is also contemplated within the scope of this invention that the nucleic acid probe assays will employ a cocktail of nucleic acid probes capable of detecting TMPRSS2 genes. Thus, in one example to detect the presence of TMPRSS2 in a cell sample, more than one probe complementary to TMPRSS2 is employed and in particular the number of different probes is alternatively 2, 3, or 5 different nucleic acid probe sequences. In another example, to detect the presence of mutations in the TMPRSS2 gene sequence in a patient, more than one probe complementary to TMPRSS2 is employed where the cocktail includes probes capable of binding to the allele-specific mutations identified in populations of patients with alterations in TMPRSS2. In this embodiment, any number of probes can be used.

It is further contemplated within the scope of this invention that the nucleic acid probe assays of this invention will employ the recently developed nucleic acid microchip technology which utilizes an array of many thousands of probes bound to a chip to analyze a sample. This method thus analyzes the sample simultaneously using all of the probes which are bound to the microchip. For published examples of this technology see Hacia et al., 1996; Shoemaker et al., 1996; Chee et al., 1996; Lockhart et al., 1996; DeRisi et al., 1996; Lipshutz et al., 1995.

Methods of Use: Peptide Diagnosis and Diagnostic Kits

The neoplastic condition of lesions can also be detected on the basis of the alteration of wild-type TMPRSS2 polypeptide. Such alterations can be determined by sequence analysis in accordance with conventional techniques. More preferably, antibodies (polyclonal or monoclonal) are used to detect differences in or the absence of TMPRSS2 peptides. In a preferred embodiment of the invention, antibodies will immunoprecipitate TMPRSS2 proteins from solution as well as react with TMPRSS2 protein on Western or immunoblots of polyacrylamide gels. In another preferred embodiment, antibodies will detect TMPRSS2 proteins in paraffin or frozen tissue sections, using immunocytochemical techniques. Techniques for raising and purifying antibodies are well known in the art, and any such techniques may be chosen to achieve the preparation of the invention.

Preferred embodiments relating to methods for detecting TMPRSS2 or its mutations include enzyme linked immunosorbent assays (ELISA), radioimmunoassays (RIA), immunoradiometric assays (IRMA) and immunoenzymatic assays (IEMA), including sandwich assays using monoclonal and/ or polyclonal antibodies. Exemplary sandwich assays are described by David et al., in U.S. Pat. Nos. 4,376,110 and 4,486,530, hereby incorporated by reference, and exemplified in Example 7.

Methods of Use: Drug Screening

This invention is particularly useful for screening compounds by using the TMPRSS2 polypeptide or binding fragment thereof in any of a variety of drug screening techniques, such as those described herein and in published PCT application WO 97/02048.

The TMPRSS2 polypeptide or fragment employed in such a test may either be free in solution, affixed to a solid support, or borne on a cell surface. One method of drug screening utilizes eukaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a TMPRSS2 polypeptide or fragment and the agent being tested, or examine the degree to which the formation of a complex between a TMPRSS2 polypeptide or fragment and a known ligand (e.g., LDL or $Ca^{+2}$), is aided or interfered with by the agent being tested.

Thus, the present invention provides methods of screening for drugs comprising contacting such an agent with a TMPRSS2 polypeptide or fragment thereof and assaying (i) for the presence of a complex between the agent and the TMPRSS2 polypeptide or fragment, or (ii) for the presence of a complex between the TMPRSS2 polypeptide or fragment and a ligand, by methods well known in the art. In such competitive binding assays the TMPRSS2 polypeptide or fragment is typically labeled. Free TMPRSS2 polypeptide or fragment is separated from that present in a protein:protein complex, and the amount of free (i.e., uncomplexed) label is a measure of the binding of the agent being tested to TMPRSS2 or its interference with or promotion of TMPRSS2:ligand binding, respectively. One may also measure the amount of bound, rather than free, TMPRSS2. It is also possible to label the ligand rather than the TMPRSS2 and to measure the amount of ligand binding to TMPRSS2 in the presence and in the absence of the drug being tested.

Another technique for drug screening provides high throughput screening for compounds having suitable binding affinity to the TMPRSS2 polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with TMPRSS2 polypeptide and washed. Bound TMPRSS2 polypeptide is then detected by methods well known in the art.

Purified TMPRSS2 can be coated directly onto plates for use in the aforementioned drug screening techniques. However, non-neutralizing antibodies to the polypeptide can be used to capture antibodies to immobilize the TMPRSS2 polypeptide on the solid phase.

This invention also contemplates the use of competitive drug screening assays in which neutralizing antibodies capable of specifically binding the TMPRSS2 polypeptide compete with a test compound for binding to the TMPRSS2 polypeptide or fragments thereof. In this manner, the antibodies can be used to detect the presence of any peptide which shares one or more antigenic determinants of the TMPRSS2 polypeptide.

The above screening methods are not limited to assays employing only TMPRSS2 but are also applicable to studying TMPRSS2-protein complexes. The effect of drugs on the activity of this complex, especially when either protein contains a mutation, is analyzed.

In accordance with these methods, the following assays are examples of assays which can be used for screening for drug candidates.

A mutant TMPRSS2 (per se or as part of a fusion protein) is mixed with a wild-type protein (per se or as part of a fusion protein) to which wild-type TMPRSS2 binds. This mixing is performed in both the presence of a drug and the absence of the drug, and the amount of binding of the mutant TMPRSS2 with the wild-type protein is measured. If the amount of the binding is more in the presence of said drug than in the absence of said drug, the drug is a drug candidate for treating cancer resulting from a mutation in TMPRSS2.

A mutant protein, which as a wild-type protein binds to TMPRSS2 (per se or as part of a fusion protein) is mixed with a wild-type TMPRSS2 (per se or as part of a fusion protein). This mixing is performed in both the presence of a drug and the absence of the drug, and the amount of binding of the mutant protein with the wild-type TMPRSS2 is measured. If the amount of the binding is more in the presence of said drug than in the absence of said drug, the drug is a drug candidate for treating cancer resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993). This system may be used as a coarse screen prior to testing a substance for actual ability to modulate activity of the polypeptide. Alternatively, the screen could be used to screen test substances for binding to a TMPRSS2 specific binding partner, or to find mimetics of the TMPRSS2 polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of cancer, use of such a substance in the manufacture of a composition for administration, e.g., for treatment of cancer, and a method of making a pharmaceutical composition comprising admixing such a substance with a pharmaceutically acceptable excipient, vehicle or carrier, and optionally other ingredients.

A substance identified using as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Rational Drug Design

The goal of rational drug design is to produce structural analogs of biologically active polypeptides of interest or of small molecules with which they interact (e.g., agonists, antagonists, inhibitors or enhancers) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., TMPRSS2) or, for example, of a TMPRSS2-substrate or TMPRSS2-ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., TMPRSS2) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved TMPRSS2 activity or stability or which act as enhancers, inhibitors, agonists, antagonists, etc. of TMPRSS2 activity. By virtue of the availability of cloned TMPRSS2 sequences, sufficient amounts of the TMPRSS2 polypeptide may be made available to perform such analytical studies as x-ray crystallography. In addition, the knowledge of the TMPRSS2 protein sequence provided herein will guide those employing computer modeling techniques in place of, or in addition to x-ray crystallography.

Methods of Use: Gene Therapy

According to the present invention, a method is also provided of supplying wild-type TMPRSS2 function to a cell which carries a mutant TMPRSS2 allele. Supplying such a function should suppress neoplastic growth of the recipient cells. The wild-type TMPRSS2 gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant TMPRSS2 allele, the gene portion should encode a part of the TMPRSS2 protein which is required for non-neoplastic growth of the cell. More preferred is the situation where the wild-type TMPRSS2 gene or a part thereof is introduced into the mutant cell in such a way that it recombines with the endogenous mutant TMPRSS2 gene present in the cell. Such recombination requires a double recombination event which results in the correction of the TMPRSS2 gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner. Cells transformed with the wild-type TMPRSS2 gene can be used as model systems to study cancer remission and drug treatments which promote such remission.

As generally discussed above, the TMPRSS2 gene or fragment, where applicable, may be employed in gene therapy methods in order to increase the amount of the expression products of such genes in cancer cells. Such gene therapy is particularly appropriate for use in both cancerous and pre-cancerous cells, in which the level of TMPRSS2 polypeptide is absent or diminished compared to normal cells. It may also be useful to increase the level of expression of a given TMPRSS2 gene even in those tumor cells in which the mutant gene is expressed at a "normal" level, but the gene product is not fully functional.

Gene therapy would be carried out according to generally accepted methods, for example, as described by Friedman (1991) or Culver (1996). Cells from a patient's tumor would be first analyzed by the diagnostic methods described above, to ascertain the production of TMPRSS2 polypeptide in the tumor cells. A virus or plasmid vector, containing a copy of the TMPRSS2 gene linked to expression control elements is prepared. The vector may be capable of replicating inside the tumor cells. Suitable vectors are known, such as disclosed in U.S. Pat. No. 5,252,479, PCT published application WO 93/07282 and U.S. Pat. No. 5,691,198. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for preparing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human (Shimada et al., 1991; Helseth et al., 1990; Page et al., 1990; Buchschacher and Panganiban, 1992) origin. Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1991; Curiel et al., 1992). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors, see Schneider et al. (1998) and U.S. Pat. No. 5,691,198.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes TMPRSS2, expression will produce TMPRSS2. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to brain tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a TMPRSS2 susceptibility allele are treated with a gene delivery vehicle such that some or all of their precursor cells receive at least one additional copy of a functional normal TMPRSS2 allele. In this step, the treated individuals have reduced risk of cancer to the extent that the effect of the susceptible allele has been countered by the presence of the normal allele.

Methods of Use: Peptide Therapy

Peptides which have TMPRSS2 activity can be supplied to cells which carry mutant or missing TMPRSS2 alleles. The sequence of the TMPRSS2 protein is disclosed (SEQ ID NO:2). Protein can be produced by expression of the cDNA sequence in bacteria, for example, using known expression vectors. Alternatively, TMPRSS2 polypeptide can be extracted from TMPRSS2-producing mammalian cells. In addition, the techniques of synthetic chemistry can be employed to synthesize TMPRSS2 protein. Any of such techniques can provide the preparation of the present invention which comprises the TMPRSS2 protein. The preparation is substantially free of other human proteins. This is most readily accomplished by synthesis in a microorganism or in vitro.

Active TMPRSS2 molecules can be introduced into cells by microinjection or by use of liposomes, for example. Alternatively, some active molecules may be taken up by cells, actively or by diffusion. Extracellular application of the TMPRSS2 gene product may be sufficient to affect tumor growth. Supply of molecules with TMPRSS2 activity should lead to partial reversal of the neoplastic state. Other molecules with TMPRSS2 activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant TMPRSS2 allele can be used as model systems to study and test for substances which have potential as therapeutic agents. The cells are typically cultured epithelial cells. These may be isolated from individuals with TMPRSS2 mutations, either somatic or germline. Alternatively, the cell line can be engineered to carry the mutation in the TMPRSS2 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant TMPRSS2 alleles, usually from a second animal species, as well as insertion of disrupted homologous genes. Alternatively, the endogenous TMPRSS2 gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

The identification of the association between the TMPRSS2 gene deletion and mutations and cancer permits the early presymptomatic screening of individuals to identify those at risk for developing cancer. To identify such individuals, TMPRSS2 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal TMPRSS2 gene or appropriate fragment (coding sequence or genomic sequence) are determined and then compared, or (2) the RNA transcripts of the TMPRSS2 gene or gene fragment are hybridized to single stranded whole genomic DNA from an individual to be tested, and the resulting heteroduplex is treated with ribonuclease A (RNase A) and run on a denaturing gel to detect the location of any mismatches. Two of these methods can be carried out according to the following procedures.

The alleles of the TMPRSS2 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal TMPRSS2 gene.

Alternatively, polymerase chain reactions (PCRs) are performed with primer pairs for the 5' region or the exons of the TMPRSS2 gene. PCRs can also be performed with primer pairs based on any sequence of the normal TMPRSS2 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common TMPRSS2 gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal TMPRSS2 gene and defective genes. This comparison is performed in steps using small (~500 bp) restriction fragments of the TMPRSS2 gene as the probe. First, the TMPRSS2 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the TMPRSS2 gene fragments are transcribed in vitro using the SP6 transcription system, well known in the art, in the presence of [$\alpha$-$^{32}$P] GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the TMPRSS2 fragment and the TMPRSS2 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the TMPRSS2 gene and the consequent presence of cancer. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for cancer at, or even before, birth. Finally, this invention changes our understanding of the cause and treatment of cancer.

Pharmaceutical Compositions and Routes of Administration

The TMPRSS2 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The present invention is described by reference to the following Examples, which are offered by way of illustration and are not intended to limit the invention in any manner. Standard techniques well known in the art or the techniques specifically described below were utilized.

EXAMPLE 1

Identification of a Homozygous Deletion in a Pancreatic Carcinoma Cell Line

A panel of 186 cell lines was screened for a homozygous deletion of the gene TMPRSS2 (GenBank Accession No. U75329). The screening was performed by using various sets of primer pairs to perform PCR and then determining whether an amplified product was formed. See Green and Olson (1990) for the use of STSs in genome mapping and see Vollrath et al. (1992) for a method of deletion mapping using STSs. Homozygous deletion searches were performed as follows: Total genomic DNA was purified from cancer cell lines using the Easy-DNA kit (Invitrogen). Using the cell line DNAs as templates, 20 μL PCR amplifications were performed with either TaqPlus (Stratagene) or AmpliTaq Gold (Perkin Elmer) and subsequently fractionated on 2–3% Nu Sieve (FMC Bioproducts) agarose gels. In general, the PCR conditions used were an initial denaturation step at 95° C. for 1 minute (TaqPlus) or 10 minutes (AmpliTaq Gold), followed by 35 cycles of denaturation at 96° C. for 12 seconds, annealing at 55° C. for 15 seconds and extension at 72° C. for 45 seconds. The homozygous deletion in BxPC3 was detected and confirmed by using the STS primer pairs shown in Table II. None of the 5 pairs of primers resulted in formation of an amplification product when used in PCR reactions with the BxPC3 cell line. The remaining cell lines all yielded appropriately sized amplification products. Table II indicates the region of TMPRSS2 which is to be amplified by each primer pair. The base numbers shown are the bases of SEQ ID NO:29 which is identical to GenBank Accession No. U75329.

gene corresponding to the primers are shown in the column labeled "Bases of SEQ ID NO:29". SEQ ID NO:29 is identical to GenBank Accession No. U75329. The primers for the secondary amplification reactions all included M13 tails. These tails are 5'-GTTTTCCCAGTCACGACG-3' (SEQ ID NO:30) for the forward primer and 5'-AGGAAACAGCTATGACCAT-3' (SEQ ID NO:31) for the reverse primer.

The sequencing results indicate that the reported sequence of TMPRSS2 (Paoloni-Giacobino et al., 1997) has some base errors. These differences are shown in Table IV.

In addition, it was determined that base 478 of SEQ ID NO:1 (base 534 of SEQ ID NO:29) is allelic for G and A with G being the more common allele, not A as had been reported in the literature. When G is present the codon is that for Val and when A is present the codon is for Met. Base 777 of SEQ ID NO:1 (base 833 of SEQ ID NO:29) is allelic for C and T with C being the more common allele, not T as had been reported in the literature. This is a silent polymorphism. Base 768 of SEQ ID NO:1 (base 824 of SEQ ID NO:29) was

TABLE II

| Primer | Sequence | SEQ ID NO: | Tm | Amplified Region (bases of SEQ ID NO:29) |
|---|---|---|---|---|
| tmprss2F | TCCACATGGTCTTCGTCCTTG | 3 | 64 | 3' untranslated region |
| tmprss2R | TTGACCGCCAGTGCCCACAAC | 4 | 68 | (bases 1536–1784) |
| tmprssF2 | CCCGTGCATGATTTACTCTTAG | 5 | 64 | 3' untranslated region |
| tmprssR2 | GCTCCATGCTCATCCAAAATTG | 6 | 64 | (bases 1597–1872) |
| tmprssF3 | AGGCAAACGGCTAATCCACATG | 7 | 66 | final 4 codons into the 3' untranslated region |
| tmprssR3 | AGTGCCAAAGCCAGACAAGTTC | 8 | 66 | (bases 1522–1677) |
| tmprssF4 | ACATTGGGTGGGGCTCCTGG | 9 | 66 | 3' untranslated region |
| tmprssR4 | AACTGAGCATCCTTGATTTCCC | 10 | 64 | (bases 2220–2410) |
| tmprssF7 | GACCTTACTATGAAAACCATGG | 11 | 62 | coding region near 5' end (amino acids 1.2–46) |
| tmprssR7 | GGGTAGTACTGAGCCGGATGC | 12 | 68 | (bases 91–193) |

EXAMPLE 2

Sequencing of TMPRSS2 cDNA

The TMPRSS2 cDNA was sequenced from 64 tumor cell lines. To accomplish this, cDNA was prepared and amplified in a first round of PCR using the primer pairs of SEQ ID NOs:13 and 14 or SEQ ID NOs:21 and 22 as shown in Table III. This primary reaction was performed for 26 cycles. Following this initial amplification, a second round of PCR was performed with nested primer pairs, i.e., using secondary primer pairs internal to the initial primer pairs. These secondary primers are shown in Table III. The regions of the found here to be allelic for C and T with C being the more common allele. This is a silent polymorphism. Base 834 of SEQ ID NO:1 (base 890 of SEQ ID NO:29) was found here to be allelic for C and T with C being the more common allele. This is a silent polymorphism and the C allele has been seen only in testis cell line Tera1. Finally, base 625 of SEQ ID NO:1 (base 681 of SEQ ID NO:29) is allelic for T and A with T being the more common allele. The A allele was seen only in breast tumor cell line BT483 which was heterozygous for the allele. The polymorphisms at bases 478, 768 and 777 of SEQ ID NO:1 were seen in several different cell lines.

TABLE III

| Name | PCR Primers | SEQ ID NO: | $T_m$ | Type of Primer | Bases of SEQ ID NO:29 |
|---|---|---|---|---|---|
| 1A | GTCATATTGAACATTCCAGATACCT | 13 | 68 | Primary | 1–25 |
| 1P | GGTATCCGGCTCCATAGAACATG | 14 | 70 | Primary | 1013–1035 |
| 1B | GTTTTCCCAGTCACGACGGATACCTATCATTACTCGATG | 15 | 58 | Secondary | 19–39 |
| 1Q | AGGAAACAGCTATGACCATGTCAAGGTGATGCACAGTGCT | 16 | 64 | Secondary | 305–325 |
| 1C | GTTTTCCCAGTCACGACGTCTGCACGCAGCCCAAATCC | 17 | 64 | Secondary | 250–269 |
| 1R | AGGAAACAGCTATGACCATCAGGGTGCCAGGACTTCCTC | 18 | 66 | Secondary | 548–567 |
| 1D | GTTTTCCCAGTCACGACGGTGTGTTCGCCTCTACGGAC | 19 | 64 | Secondary | 497–516 |
| 1S | AGGAAACAGCTATGACCATTTGAGTTCAAGTTGACCCC | 20 | 60 | Secondary | 788–807 |

TABLE III-continued

| Name PCR Primers | | SEQ ID NO: | $T_m$ | Type of Primer | Bases of SEQ ID NO:29 |
|---|---|---|---|---|---|
| 2A | TGCAGGGACATGGGCTATAAGAAG | 21 | 68 | Primary | 609–631 |
| 2P | TTAGGGAGAGCAGGCTGGGCA | 22 | 68 | Primary | 1712–1732 |
| 2B | GTTTTCCCAGTCACGACGCCACAGTGATGCCTGTTCTTC | 23 | 64 | Secondary | 734–754 |
| 2Q | AGGAAACAGCTATGACCATTTGTACTTGGTATCCGGCTC | 24 | 64 | Secondary | 1023–1043 |
| 2C | GTTTTCCCAGTCACGACGCATGGCATTGGACGGCATTTG | 25 | 64 | Secondary | 970–990 |
| 2R | AGGAAACAGCTATGACCATCATAGACATATCTGCTGTTGC | 26 | 60 | Secondary | 1285–1305 |
| 2D | GTTTTCCCAGTCACGACGCTCAGAAGTGCTGAACGCTGC | 27 | 66 | Secondary | 1235–1255 |
| 2S | AGGAAACAGCTATGACCATCCAGCCCCATTGTTTTCTTGT | 28 | 62 | Secondary | 1567–1587 |

TABLE IV

| Base in SEQ ID NO:1 | Base in SEQ ID NO:29 | Base and codon reported in literature | Base and codon as determined herein |
|---|---|---|---|
| 724 | 780 | T (Leu) | A (Ile) |
| 985 | 1041 | C (Gln) | G (Glu) |
| 1347 | 1403 | C (Asn) | G (Lys) |
| 1466 | 1522 | A (Lys) | G (Arg) |
| 1471 | 1527 | A (Asn) | G (Asp) |

EXAMPLE 3

Biochemical Activity of TMPRSS2 Variants

TMPRSS2 contains several different known domains which are correlated with a variety of activities. Variants of TMPRSS2, e.g., with point mutations, deletions, insertions or other variations, can be tested for these various activities. The activities which can be tested include protease activity and binding of LDLs and calcium as well as binding to cell surface or extracellular molecules (Paoloni-Giacobino et al., 1997). Such assays can determine whether a specific variant of TMPRSS2 has normal or abnormal (too high or too low) activity for the function being assayed and these results can be compared with other data to indicate whether such variants are correlated with the presence of cancer or a tumor. Such assays may indicate that only one of the activities of TMPRSS2 is correlated with cancer and this activity would then be focused upon for screening for drugs for treating the cancer. More than one of the activities of TMPRSS2 may be found to be associated with cancer in which event all such activities would be targets for treatment with drugs.

EXAMPLE 4

Two Step Assay to Detect the Presence of TMPRSS2 in a Sample

Patient sample is processed according to the method disclosed by Antonarakis et al. (1985), separated through a 1% agarose gel and transferred to nylon membrane for Southern blot analysis. Membranes are UV cross linked at 150 mJ using a GS Gene Linker (Bio-Rad). A TMPRSS2 probe is subcloned into pTZ18U. The phagemids are transformed into *E. coli* MV1190 infected with M13KO7 helper phage (Bio-Rad, Richmond, Calif.). Single stranded DNA is isolated according to standard procedures (see Sambrook et al., 1989).

Blots are prehybridized for 15–30 min at 65° C. in 7% sodium dodecyl sulfate (SDS) in 0.5 M $NaPO_4$. The methods follow those described by Nguyen, et al., 1992. The blots are hybridized overnight at 65° C. in 7% SDS, 0.5 M $NaPO_4$ with 25–50 ng/ml single stranded probe DNA. Post-hybridization washes consist of two 30 min washes in 5% SDS, 40 mM $NaPO_4$ at 65° C., followed by two 30-min washes in 1% SDS, 40 mM $NaPO_4$ at 65° C.

Next the blots are rinsed with phosphate buffered saline (pH 6.8) for 5 min at room temperature and incubated with 0.2% casein in PBS for 30–60 min. at room temperature and rinsed in PBS for 5 min. The blots are then preincubated for 5–10 minutes in a shaking water bath at 45° C. with hybridization buffer consisting of 6 M urea, 0.3 M NaCl, and 5×Denhardt's solution (see Sambrook, et al., 1989). The buffer is removed and replaced with 50–75 $\mu$l/cm$^2$ fresh hybridization buffer plus 2.5 nM of the covalently cross-linked oligonucleotide-alkaline phosphatase conjugate with the nucleotide sequence complementary to the universal primer site (UP-AP, Bio-Rad). The blots are hybridized for 20–30 min at 45° C. and post hybridization washes are incubated at 45° C. as two 10 min washes in 6 M urea, 1×standard saline citrate (SSC), 0.1% SDS and one 10 min wash in 1×SSC, 0.1% Triton®X-100. The blots are rinsed for 10 min at room temp. with 1×SSC.

Blots are incubated for 10 min at room temperature with shaking in the substrate buffer consisting of 0.1 M diethanolamine, 1 mM $MgCl_2$, 0.02% sodium azide, pH 10.0. Individual blots are placed in heat sealable bags with substrate buffer and 0.2 mM AMPPD (3-(2'-spiroadamantane)-4-methoxy-4-(3'-phosphoryloxy)phenyl-1,2-dioxetane, disodium salt, Bio-Rad). After a 20 min incubation at room temperature with shaking, the excess AMPPD solution is removed. The blot is exposed to X-ray film overnight. Positive bands indicate the presence of TMPRSS2.

EXAMPLE 5

Generation of Polyclonal Antibody against TMPRSS2

Segments of TMPRSS2 coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of TMPRSS2 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. The identification of the protein as the TMPRSS2 fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the TMPRSS2 gene. These antibodies, in conjunction with antibodies to wild type TMPRSS2, are used to detect the presence and the relative level of the mutant forms in various tissues and biological fluids.

EXAMPLE 6

Generation of Monoclonal Antibodies Specific for TMPRSS2

Monoclonal antibodies are generated according to the following protocol. Mice are immunized with immunogen comprising intact TMPRSS2 or TMPRSS2 peptides (wild type or mutant) conjugated to keyhole limpet hemocyanin using glutaraldehyde or EDC as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of TMPRSS2 specific antibodies by ELISA or RIA using wild type or mutant TMPRSS2 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 7

Sandwich Assay for TMPRSS2

Monoclonal antibody is attached to a solid surface such as a plate, tube, bead, or particle. Preferably, the antibody is attached to the well surface of a 96-well ELISA plate. 100 µl sample (e.g., serum, urine, tissue cytosol) containing the TMPRSS2 peptide/protein (wild-type or mutants) is added to the solid phase antibody. The sample is incubated for 2 hrs at room temperature. Next the sample fluid is decanted, and the solid phase is washed with buffer to remove unbound material. 100 µl of a second monoclonal antibody (to a different determinant on the MKK3 peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of TMPRSS2 peptide/protein present in the sample, is quantified. Separate assays are performed using monoclonal antibodies which are specific for the wild-type TMPRSS2 as well as monoclonal antibodies specific for each of the mutations identified in TMPRSS2.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Altschul S F, et al. (1997). *Nucl. Acids Res.* 25:3389–3402.
American Cancer Society (1992). In *Cancer Facts and Figures*—1992.
Anand R (1992). *Techniques for the Analysis of Complex Genomes* (Academic Press).
Anderson W F, et al. (1980). *Proc. Natl. Acad. Sci. USA* 77:5399–5403.
Anderson J A, et al. (1992). *J. Otolaryngology* 21:321.
Antonarakis S E, et al. (1985). *New Engl. J. Med.* 313:842–848.
Ausubel F M, et al. (1992). *Current Protocols in Molecular Biology* (John Wiley and Sons, New York, N.Y.).
Bandyopadhyay P K and Temin H M (1984), *Mol. Cell. Biol.* 4:749–754.
Bartel P L, et al. (1993). "Using the 2-hybrid system to detect protein-protein interactions." In *Cellular Interactions in Development: A Practical Approach*, Oxford University Press, pp. 153–179.
Berglund P, et al. (1993). *Biotechnology* 11:916–920.
Beaucage S L and Caruthers M H (1981). *Tetra. Letts.* 22:1859–1862.
Berkner K L (1992). *Curr. Top. Microbiol. Immunol.* 158:39–66.
Berkner K L, et al. (1988). *BioTechniques* 6:616–629.
Borman S (1996). *Chemical & Engineering News*, December 9 issue, pp. 42–43.
Breakefield X O and Geller A I (1987). *Mol. Neurobiol.* 1:339–371.
Brinster R L, et al. (1981). *Cell* 27:223–231.
Buchschacher G L and Panganiban A T (1992). *J. Virol.* 66:2731–2739.
Cannon-Albright L A, et al. (1992). *Science* 258:1148–1152.
Capecchi M R (1989). *Science* 244:1288.
Cariello N F (1988). *Am. J. Human Genetics* 42:726–734.
Chee M, et al. (1996). *Science* 274:610–614.
Chen Y-R et al. (1996). *J. Biol. Chem.* 271:631–634.
Cheng J Q, et al. (1993). *Cancer Res.* 53:4761.
Conner B J, et al. (1983). *Proc. Nat. Acad. Sci. USA* 80:278–282.
Costantini F and Lacy E (1981). *Nature* 294:92–94.
Cotten M, et al. (1990). *Proc. Natl. Acad Sci. USA* 87:4033–4037.
Cotton R G, et al. (1988). *Proc. Nat. Acad. Sci. USA* 85:4397–4401.
Culver K W, et al. (1992). *Science* 256:1550–1552.
Culver K (1996). *Gene Therapy: A Primer for Physicians*, 2nd Ed., Mary Ann Liebert.

Curiel D T, et al. (1991). *Proc. Natl. Acad. Sci. USA* 88:8850–8854.
Curiel D T, et al. (1992). *Hum. Gene Ther.* 3:147–154.
Cuvillier O, et al. (1996). *Nature* 381:800–803.
Dérijard B, et al. (1995). *Science* 267:682–685.
Deutscher M (1990). *Meth. Enzymology* 182:83–89 (Academic Press, San Diego).
DeRisi J, et al. (1996). *Nature Genetics* 14:457–460.
Diaz M O, et al. (1988). *Proc. Natl. Acad. Sci. USA* 85: 5259–5263.
Donehower L A, et al. (1992). *Nature* 356:215.
Editorial (1996). *Nature Genetics* 14:367–370.
Elghanian R, et al. (1997). *Science* 277:1078–1081.
*Enhancers and Eukaryotic Gene Expression*, Cold Spring Harbor Press, Cold Spring Harbor, N.Y. (1983).
Erickson J, et al. (1990). *Science* 249:527–533.
Ewen M E, et al. (1993). *Cell* 73:47.
Felgner P L, et al. (1987). *Proc. Natl. Acad. Sci. USA* 84:7413–7417.
Fiers W, et al. (1978). *Nature* 273:113–120.
Fink D J, et al. (1992). *Hum. Gene Ther.* 3:11–19.
Fink D J et al. (1996). *Ann. Rev. Neurosci.* 19:265–287.
Finkelstein J, et al. (1990). *Genomics* 7:167–172.
Fodor S P A (1997). DNA Sequencing. Massively Parallel Genomics. Science 277, 393–395.
Fountain J W, et al. (1992). *Proc. Natl. Acad. Sci. USA* 89:10557–10561.
Freese A, et al. (1990). *Biochem. Pharmacol.* 40:2189–2199.
Friedman T (1991). In *Therapy for Genetic Diseases*, T. Friedman, ed., Oxford University Press, pp. 105–121.
Glover D (1985). *DNA Cloning*, I and II (Oxford Press).
Goding (1986). *Monoclonal Antibodies: Principles and Practice*, 2d ed. (Academic Press, New York).
Godowski P J, et al. (1988). *Science* 241:812–816.
Goldstein A M, et al. (1994). *Am. J. Hum. Genet.* 54:489.
Gordon J W, et al. (1980). *Proc. Natl. Acad. Sci. USA* 77:7380–7384.
Gorziglia M and Kapikian A Z (1992). *J. Virol.* 66:4407–4412.
Graham F L and van der Eb A J (1973). *Virology* 52:456–467.
Green E D and Olson M V (1990). *Science* 250:94–98.
Grompe M (1993). *Nature Genetics* 5:111–117.
Grompe M, et al. (1989). *Proc. Natl. Acad Sci. USA* 86:5855–5892.
Gruis N A, et al. (1993). *Melanoma Res.* 3:271.
Gruis N A, et al. (1995). *Am. J. Pathol.* 146:1–8.
Guthrie G and Fink G R (1991). *Guide to Yeast Genetics and Molecular Biology*, (Academic Press).
Hacia J G, et al. (1996). *Nature Genetics* 14:441–447.
Hahn S A, et al. (1996). *Science* 271:350–353.
Hannon G J and Beach D (1994). *Nature* 371:257–261.
Harlow E and Lane D (1988). *Antibodies: A Laboratory Manual*, (Cold Spring Harbor Laboratory, Cold Spring Harbor, N.Y.).
Hasty P K, et al. (1991). *Nature* 350:243.
Helseth E, et al. (1990). *J. Virol.* 64:2416–2420.
Hodgson J (1991). *Bio/Technology* 9:19–21.
Huse W D, et al. (1989). *Science* 246:1275–1281.
Innis M A, et al. (1990). *PCR Protocols: A Guide to Methods and Applications* (Academic Press, San Diego).
Jablonski E, et al. (1986). *Nucl. Acids Res.* 14:6115–6128.
Jakoby W B and Pastan I H (eds.) (1979). Cell Culture. Methods in Enzymology, volume 58 (Academic Press, Inc., Harcourt Brace Jovanovich (New York)).
James C D, et al. (1993). *Cancer Res.* 53:3674.
Jiang P, et al. (1995). *J. Mol. Evol.* 41:795–802.
Johnson P A, et al. (1992). *J. Virol.* 66:2952–2965.
Johnson, et al. (1993). "Peptide Turn Mimetics" in *Biotechnology and Pharmacy*, Pezzuto et al., eds., Chapman and Hall, New York.
Johnson N L, et al. (1996). *J. Biol. Chem.* 271:3229–3237.
Kamb A, et al. (1994). *Science* 264:436–440.
Kaneda Y, et al. (1989). *J. Biol. Chem.* 264:12126–12129.
Kanehisa M (1984). *Nucl. Acids Res.* 12:203–213.
Kinszler K W, et al. (1991). *Science* 251:1366–1370.
Knudson A G (1971). *Proc. Natl. Acad. Sci. USA* 68:820.
Knudson A G (1993). *Nature Genet.* 5:103.
Kohler G and Milstein C (1975). *Nature* 256:495–497.
Kraemer F B, et al. (1993). *J. Lipid Res.* 34:663–672.
Kubo T, et al. (1988). *FEBS Lett.* 241:119.
Kyriakis J M and Avruch J (1996). *J. Biol. Chem.* 271:24313–24316.
Kyte J and Doolittle R F (1982). *J. Mol. Bio.* 157:105–132.
Lammie G A, et al. (1991). *Oncogene,* 6:439.
Landegren U, et al. (1988). *Science* 242:229–237.
Li J, et al. (1997). *Science* 275:1943–1947.
Lim C S, et al. (1991). *Circulation* 83:2007–2011.
Lin A, et al. (1995). *Science* 268:286–290.
Lipshutz R J, et al. (1995). *Biotechniques* 19:442–447.
Liu Q, et al. (1995a). *Oncogene* 10:619–622.
Liu Q, et al. (1995b). *Oncogene* 10:1061–1067.
Lockhart D J, et al. (1996). *Nature Biotechnology* 14:1675–1680.
Lukeis R, et al. (1990). *Genes, Chromo. Cancer* 2:116–124.
Madzak C, et al. (1992). *J. Gen. Virol.* 73:1533–1536.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401–407.
Margolskee R F (1992). *Curr. Top. Microbiol. Immunol.* 158:67–95.
Martin R, et al. (1990). *BioTechniques* 9:762–768.
Marx J (1994). *Science* 263:319–321.
Matteucci M D and Caruthers M H (1981). *J. Am. Chem. Soc.* 103:3185.
Matthews J A and Kricka L J (1988). *Anal. Biochem.* 169:1.
Merrifield B (1963). *J. Am. Chem. Soc.* 85:2149–2156.
Metzger D, et al. (1988). *Nature* 334:31–36.
Middleton P G, et al. (1991). *Leukemia* 5:680–682.
Mifflin T E (1989). *Clinical Chem.* 35:1819–1825.
Miller A D (1992). *Curr. Top. Microbiol. Immunol.* 158:1–24.
Miller A D, et al. (1985). *Mol. Cell. Biol.* 5:431–437.
Miller A D, et al. (1988). *J. Virol.* 62:4337–4345.
Modrich P (1991). *Ann. Rev. Genet.* 25:229–253.
Mollenhauer J, et al. (1997). *Nature Genetics* 17:32–39.
Mombaerts P, et al. (1992). *Cell* 68:869.
Moss B (1992). *Curr. Top. Microbiol. Immunol.* 158:25–38.
Moss B (1996). *Proc. Natl. Acad. Sci. USA* 93:11341–11348.
Motokura T, et al. (1991). *Nature* 350:512.
Muzyczka N (1992). *Curr. Top. Microbiol. Immunol.* 158:97–129.
Nabel E G, et al. (1990). *Science* 249:1285–1288.
Nabel (1992). *Hum. Gene Ther.* 3:399–410.
Naldini L, et al. (1996). *Science* 272:263–267.
Nancarrow D J, et al. (1993). *Am. J. Hum. Genet.* 53:936.
Nasmyth K and Hunt T (1993). *Nature* 366:634–635.
Newton C R, et al. (1989). *Nucl. Acids Res.* 17:2503–2516.
Nguyen Q, et al. (1992). *BioTechniques* 13:116–123.
Novack D F, et al. (1986). Proc. Nat. Acad. Sci. USA 83:586–590.
Ohi S, et al. (1990). *Gene* 89:279–282.

Olopade O I, et al. (1992). *Cancer Res.* 52:2523–2529.
Olopade O I, et al. (1993). *Cancer Res.* 53:2410–2415.
Orita M, et al. (1989). *Proc. Nat. Acad. Sci. USA* 86:2776–2770.
Page K A, et al. (1990). *J. Virol.* 64:5270–5276.
Paoloni-Giacobino A, et al. (1997). *Genomics* 44:309–320.
Pellicer A, et al. (1980). *Science* 209:1414–1422.
Petropoulos C J, et al. (1992). *J. Virol.* 66:3391–3397.
Philpott K L, et al. (1992). *Science* 256:1448.
Quantin B, et al. (1992). *Proc. Natl. Acad. Sci. USA* 89:2581–2584.
*Remington's Pharmaceutical Sciences,* 18th Ed. (1990, Mack Publishing Co., Easton, Pa.).
Resnick D, et al. (1994). *Trends in Biochemical Sciences* 19:5–8.
Rigby P W J, et al. (1977). *J. Mol. Biol.* 113:237–251.
Rosenberg C L, et al. (1991). *Proc. Natl. Acad. Sci. USA* 88:9638.
Rosenfeld M A, et al. (1992). *Cell* 68:143–155.
Ruano G and Kidd K K (1989). *Nucl. Acids Res.* 17:8392.
Russell D and Hirata R (1998). *Nature Genetics* 18:323–328.
Sambrook J, et al. (1989). *Molecular Cloning: A Laboratory Manual,* 2nd Ed. (Cold Spring Harbor Laboratory, Cold Spring Harbor, N.Y.).
Scharf S J, et al. (1986). *Science* 233:1076–1078.
Schneider G, et al. (1998). *Nature Genetics* 18:180–183.
Scopes R (1982). *Protein Purification: Principles and Practice,* (Springer-Verlag, New York).
Serrano M, et al. (1993). *Nature* 366:704.
Sheffield V C, et al. (1989). *Proc. Natl. Acad Sci. USA* 86: 232–236.
Sheffield V C, et al. (1991). *Am. J. Hum. Genet.* 49:699–706.
Shenk T E, et al. (1975). *Proc. Natl. Acad Sci. USA* 72:989.
Shimada T, et al. (1991). *J. Clin. Invest.* 88:1043–1047.
Shinkai Y, et al. (1992). *Cell* 68:855.
Shoemaker D D, et al. (1996). *Nature Genetics* 14:450–456.
Snouwaert J N, et al. (1992). *Science* 257:1083.
Sorge J, et al. (1984). *Mol. Cell. Biol.* 4:1730–1737.
Steck P A, et al. (1997). *Nature Genet.* 15:356–362.
Stewart M J, et al. (1992). *Hum. Gene Ther.* 3:267–275.
Stone S, et al. (1995a). *Cancer Res.* 55:2988–2994.
Stone S, et al. (1995b). *Oncogene* 11:987–991.
Stratford-Perricaudet L D, et al. (1990). *Hum. Gene Ther.* 1:241–256.
Tavtigian S V, et al. (1996). *Nature Genet.* 12:333–337.
Valancius V and Smithies O (1991). *Mol. Cell Biol.* 11:1402.
Verheij M, et al. (1996). *Nature* 380:75–79.
Vollrath D, et al. (1992). *Science* 258:52–59.
Wagner E, et al. (1990). *Proc. Natl. Acad. Sci. USA* 87:3410–3414.
Wagner E, et al. (1991). *Proc. Natl. Acad. Sci. USA* 88:4255–4259.
Wang C Y and Huang L (1989). *Biochemisty* 28:9508–9514.
Wartell R M, et al. (1990). *Nucl. Acids Res.* 18:2699–2705.
Waskiewicz A J and Cooper J (1995). *Curr. Opin. Cell Biol.* 7:798–805.
Wells J A (1991). *Methods Enzymol.* 202:390–411.
Wetmur J G and Davidson N (1968). *J. Mol. Biol.* 31:349–370.
White R and Lalouel J M (1988). *Annu. Rev. Genet.* 22:259–279.
White M B, et al. (1992). *Genomics* 12:301–306.
Whitney G S, et al. (1995). *J. Biol. Chem.* 270:18187–18190.
Wilkinson G W and Akrigg A (1992). *Nucleic Acids Res.* 20:2233–2239.
Withers D A, et al. (1991). *Mol. Cell. Biol.* 11:4846.
Wolff J A, et al. (1990). *Science* 247:1465–1468.
Wolff J A, et al. (1991). *BioTechniques* 11:474–485.
Wooster R, et al. (1995). *Nature* 378:789–792.
Wu D Y and Wallace R B (1989). *Genomics* 4:560–569.
Wu C H, et al. (1989). *J. Biol. Chem.* 264:16985–16987.
Wu G Y, et al. (1991). *J. Biol. Chem.* 266:14338–14342.
Xia Z, et al. (1995). *Science* 270:1326–1331.
Yan M, et al. (1994). *Nature* 372:798–800.
Zenke M, et al. (1990). *Proc. Natl. Acad. Sci. USA* 87:3655–3659.

List of Patents and Patent Applications

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,554,101
U.S. Pat. No. 4,683,195
U.S. Pat. No. 4,683,202
U.S. Pat. No. 4,816,567
U.S. Pat. No. 4,868,105
U.S. Pat. No. 5,252,479
U.S. Pat. No. 5,550,050
U.S. Pat. No. 5,691,198
EPO Publication No. 225,807
European Pat. No. Application Publication No. 0332435
Hitzeman et al., EP 73,675A
EP 425,731A
PCT published application WO 84/03564
PCT published application WO 90/07936
PCT published application WO 92/19195
PCT published application WO 93/07282
PCT published application WO 94/25503
PCT published application WO 95/01203
PCT published application WO 95/05452
PCT published application WO 96/02286
PCT published application WO 96/11698
PCT published application WO 96/40871
PCT published application WO 96/40959
PCT published application WO 97/02048
PCT published application WO 97/12635

What is claimed is:

1. An isolated DNA comprising a polymorphic variant of SEQ ID NO:1 wherein said polymorphic variant of SEQ ID NO:1 comprises one or more polymorphisms selected from the group consisting of G or A at base 478, C or T at base 777, C or T at base 768, C or T at base 834, and T or A at base 625.

* * * * *